(12) United States Patent
Sakoda et al.

(10) Patent No.: US 8,574,173 B2
(45) Date of Patent: Nov. 5, 2013

(54) MOTOR FUNCTION ESTIMATING SYSTEM, MOTOR FUNCTION ESTIMATING METHOD AND PROGRAM

(75) Inventors: Saburo Sakoda, Ashiya (JP); Toshio Tsuji, Higashi-hiroshima (JP); Keisuke Shima, Fuchu (JP); Masaru Yokoe, Suita (JP); Yuko Sano, Kokubunji (JP); Akihiko Kandori, Tokyo (JP); Tsuyoshi Miyashita, Tsurugshima (JP)

(73) Assignee: Hitachi Consumer Electronics Co., Ltd., Tokyo (JP)

( * ) Notice: Subject to any disclaimer, the term of this patent is extended or adjusted under 35 U.S.C. 154(b) by 452 days.

(21) Appl. No.: 12/854,357

(22) Filed: Aug. 11, 2010

(65) Prior Publication Data

US 2011/0054361 A1    Mar. 3, 2011

(30) Foreign Application Priority Data

Aug. 27, 2009    (JP) .................................. 2009-196400

(51) Int. Cl.
    *A61B 5/103*    (2006.01)
    *A61B 5/117*    (2006.01)
    *A61B 5/00*    (2006.01)
    *G01L 5/16*    (2006.01)

(52) U.S. Cl.
    USPC .......... 600/595; 600/587; 73/865.3; 73/865.4

(58) Field of Classification Search
    USPC ..................... 600/587, 595; 73/865.3, 865.4
    See application file for complete search history.

(56) References Cited

U.S. PATENT DOCUMENTS

| 7,419,473 B2 * | 9/2008 | Kandori et al. ............... 600/595 |
| 2008/0238414 A1 | 10/2008 | Miyashita et al. |

FOREIGN PATENT DOCUMENTS

| JP | 2000-102523 A | 4/2000 |
| JP | 2003-199728 A | 7/2003 |
| JP | 2004-016336 A | 1/2004 |
| JP | 2005-095197 A | 4/2005 |
| JP | 2005-143801 A | 6/2005 |
| JP | 2005-152053 A | 6/2005 |
| JP | 2006-296618 A | 11/2006 |
| JP | 2007-054597 A | 3/2007 |

(Continued)

OTHER PUBLICATIONS

Shima et al. "Measurement and Evaluation of Finger Tapping Movements Using Magnetic Sensors", 30th Annual International IEEE EMBS Conference, Aug. 20-24, 2008, pp. 5628-5631.*

(Continued)

*Primary Examiner* — Jeffrey G Hoekstra
*Assistant Examiner* — Devin Henson
(74) *Attorney, Agent, or Firm* — Mattingly & Malur, PC

(57) ABSTRACT

The motor function estimating system 1000 has a memory unit 1260, a data processing unit 1220 (analyzing section), and a display unit 1400. The memory unit 1260 memorizes waveform data about the time change of fingers tapping motion that is obtained by a motion sensor attached to a subject person who does the fingers tapping motion that is repetition of the opening and closing motion of two fingers of one hand. The data processing unit 1220 analyzes the waveform data in the memory unit 1260. The display unit 1400 displays an analysis result. The data processing unit 1220 creates motion waveform based on waveform data, and plural characteristics based on the motion waveform. The data processing unit 1220 creates a motion disorder synthesis value that represents degree of motion disorder of the subject person by revising each of the plural characteristics based on characteristics of every age and synthesizing them.

15 Claims, 30 Drawing Sheets

(56) References Cited

FOREIGN PATENT DOCUMENTS

| | | |
|---|---|---|
| JP | 2008-158748 A | 7/2008 |
| JP | 2008-246126 A | 10/2008 |
| JP | 2009-136667 A | 6/2009 |

OTHER PUBLICATIONS

Homann et al. "Influence of age, gender, education, and dexterity on upper limb motor performance in Parkinsonian patients and healthy controls", Journal of Neural Transmission, 2003, vol. 110, Issue 8, pp. 885-897.*

A. Kandori et al., Quantitative magnetic detection of finger movements in patients with Parkinson's disease, Neuroscience Research, 2004, pp. 253-260, vol. 49, No. 2, Japan.

M. Murata et al., Evaluation of drug efficacy for Parkinson's disease using finger tapping device, The second motor function meeting for the study, Nov. 16, 2007, 2 pp., Japan.

* cited by examiner

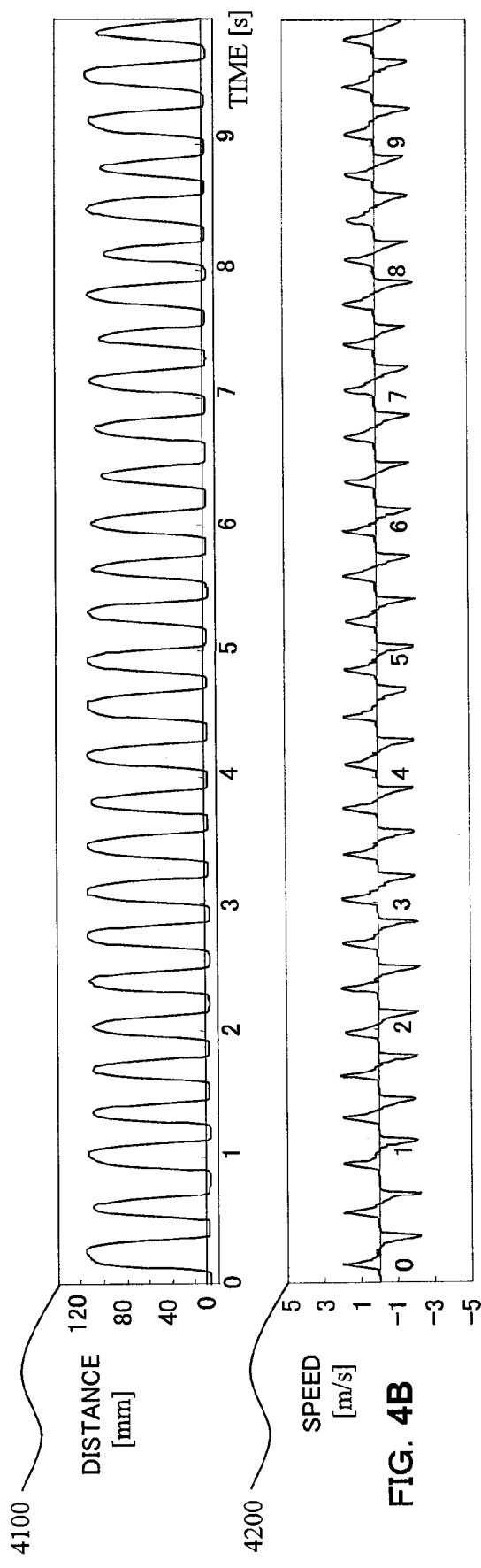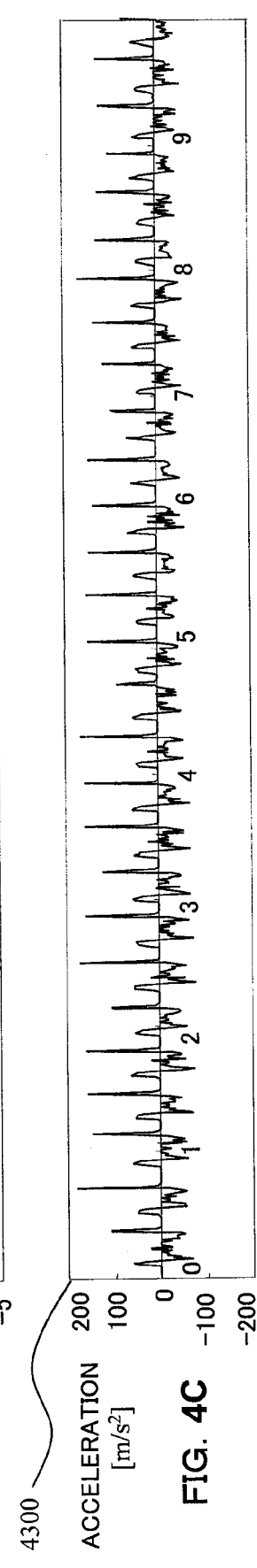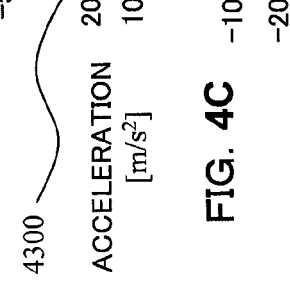

FIG.5A

| CHARACTERISTICS NUMBER | NAME | DEFINITION |
|---|---|---|
| 5001 | MAXIMUM AMPLITUDE ON DISTANCE WAVEFORM | MAXIMUM VALUE OF LOCAL MAXIMUM VALUES ON DISTANCE WAVEFORM IN WHOLE MEASUREMENT TIME |
| 5002 | TOTAL MOTION DISTANCE ON DISTANCE WAVEFORM | VALUE OBTAINED BY INTEGRATING ABSOLUTE VALUE OF DIFFERENTIAL CALCULUS VALUE ON DISTANCE WAVEFORM IN WHOLE MEASUREMENT TIME |
| 5003 | MAXIMUM VALUE ON DISTANCE WAVEFORM AT CALIBRATION | DISTANCE VALUE OBTAINED BY CALCULATING VOLTAGE VALUE THAT IS MEASURED WHEN A FOREFINGER AND A THUMB ARE OPENED MOST AT CALIBRATION |
| 5004 | AVERAGE OF LOCAL MAXIMUM VALUES ON DISTANCE WAVEFORM | AVERAGE OF LOCAL MAXIMUM VALUES ON DISTANCE WAVEFORM IN WHOLE MEASUREMENT TIME |
| 5005 | STANDARD DEVIATION OF LOCAL MAXIMUM VALUES ON DISTANCE WAVEFORM | STANDARD DEVIATION OF LOCAL MAXIMUM VALUES ON DISTANCE WAVEFORM IN WHOLE MEASUREMENT TIME |
| 5006 | INCLINATION OF APPROXIMATE STRAIGHT LINE AT LOCAL MAXIMUM POINT ON DISTANCE WAVEFORM | INCLINATION OF APPROXIMATE STRAIGHT LINE AT LOCAL MAXIMUM POINT ON DISTANCE WAVEFORM |
| 5007 | MAXIMUM AMPLITUDE ON DISTANCE WAVEFORM | MAXIMUM VALUE OF LOCAL MAXIMUM VALUES ON DISTANCE WAVEFORM IN WHOLE MEASUREMENT TIME |
| 5008 | AVERAGE OF MAXIMUM VALUES DURING OPENING MOTION ON SPEED WAVEFORM | AVERAGE OF MAXIMUM VALUES DURING OPENING MOTION ON SPEED WAVEFORM IN WHOLE MEASUREMENT TIME |
| 5009 | AVERAGE OF MINIMUM VALUES DURING CLOSING MOTION ON SPEED WAVEFORM | AVERAGE OF MINIMUM VALUES DURING CLOSING MOTION ON SPEED WAVEFORM IN WHOLE MEASUREMENT TIME |
| 5010 | STANDARD DEVIATION OF MAXIMUM VALUES DURING OPENING MOTION ON SPEED WAVEFORM | STANDARD DEVIATION OF MAXIMUM VALUES DURING OPENING MOTION ON SPEED WAVEFORM IN WHOLE MEASUREMENT TIME |
| 5011 | STANDARD DEVIATION OF MINIMUM VALUES DURING CLOSING MOTION ON SPEED WAVEFORM | STANDARD DEVIATION OF MINIMUM VALUES DURING CLOSING MOTION ON SPEED WAVEFORM IN WHOLE MEASUREMENT TIME |
| 5012 | ENERGY BALANCE OF SPEED WAVEFORM | RATIO SUM OF SQUARE OF SPEED WHEN SPEED IS PLUS AND SUM OF SQUARE OF SPEED WHEN SPEED IS MINUS IN WHOLE MEASUREMENT TIME |
| 5013 | TOTAL ENERGY VALUE OF SPEED WAVEFORM | TOTAL ENERGY VALUE OF SPEED WAVEFORM |
| 5014 | MAXIMUM AMPLITUDE ON ACCELERATION WAVEFORM | MAXIMUM VALUE OF LOCAL MAXIMUM VALUES ON ACCELERATION WAVEFORM IN WHOLE MEASUREMENT TIME |

FIG.5B

| CHARACTERISTICS NUMBER | NAME | DEFINITION |
|---|---|---|
| 5015 | AVERAGE OF MAXIMUM VALUES DURING OPENING MOTION ON ACCELERATION | AVERAGE OF MAXIMUM VALUES DURING OPENING MOTION ON ACCELERATION WAVEFORM IN WHOLE MEASUREMENT TIME |
| 5016 | AVERAGE OF MINIMUM VALUES DURING OPENING MOTION ON ACCELERATION | AVERAGE OF MINIMUM VALUES DURING OPENING MOTION ON ACCELERATION WAVEFORM IN WHOLE MEASUREMENT TIME |
| 5017 | AVERAGE OF MAXIMUM VALUES DURING CLOSING MOTION ON ACCELERATION | AVERAGE OF MAXIMUM VALUES DURING CLOSING MOTION ON ACCELERATION WAVEFORM IN WHOLE MEASUREMENT TIME |
| 5018 | AVERAGE OF MINIMUM VALUES DURING CLOSING MOTION ON ACCELERATION | AVERAGE OF MINIMUM VALUES DURING CLOSING MOTION ON ACCELERATION WAVEFORM IN WHOLE MEASUREMENT TIME |
| 5019 | THE NUMBER OF TAPPING TIMES | THE NUMBER OF LOCAL MINIMUM POINT ON DISTANCE WAVEFORM IN WHOLE MEASUREMENT TIME |
| 5020 | AVERAGE VALUE OF TAPPING INTERVALS | WHOLE MEASUREMENT TIME / THE NUMBER OF TAPPING TIMES (5019) |
| 5021 | AVERAGE FREQUENCY OF TAPPING INTERVALS | 1 / AVERAGE VALUE OF TAPPING INTERVALS (5020) |
| 5022 | STANDARD DEVIATION OF TAPPING INTERVALS | STANDARD DEVIATION OF LENGTHS OF CYCLE OF FINGERS TAPPING MOTION IN WHOLE MEASUREMENT TIME |
| 5023 | THE NUMBER OF ZERO CROSSING TIMES ON SPEED WAVEFORM | (THE NUMBER OF TIMES FOR WHICH SPEED CHANGES TO MINUS FROM PLUS) - (THE NUMBER OF TAPPING TIMES (5019)) IN WHOLE MEASUREMENT TIME |
| 5024 | THE NUMBER OF ZERO CROSSING TIMES ON ACCELERATION WAVEFORM | (THE NUMBER OF TIMES FOR WHICH ACCELERATION VALUE CHANGES TO MINUS FROM PLUS) - (THE NUMBER OF TAPPING TIMES (5019)) IN WHOLE MEASUREMENT TIME |
| 5025 | LOCAL STANDARD DEVIATION OF LOCAL MAXIMUM VALUES ON DISTANCE WAVEFORM | AVERAGE OF STANDARD DEVIATIONS OF N LOCAL MAXIMUM VALUES IN A ROW ON DISTANCE WAVEFORM IN WHOLE MEASUREMENT TIME |
| 5026 | LOCAL STANDARD DEVIATION OF TAPPING INTERVALS | AVERAGE OF STANDARD DEVIATIONS OF N TAPPING INTERVALS IN A ROW IN WHOLE MEASUREMENT TIME |
| 5027 | DISTORTION DEGREE OF DISTRIBUTION OF TAPPING INTERVALS | DISTORTION DEGREE OF DISTRIBUTION OF TAPPING INTERVALS IN WHOLE MEASUREMENT TIME |
| 5028 | KURTOSIS OF LOCAL MAXIMUM POINT | AVERAGE OF KURTOSISES OF LOCAL MAXIMUM POINTS ON DISTANCE WAVEFORM IN WHOLE MEASUREMENT TIME |

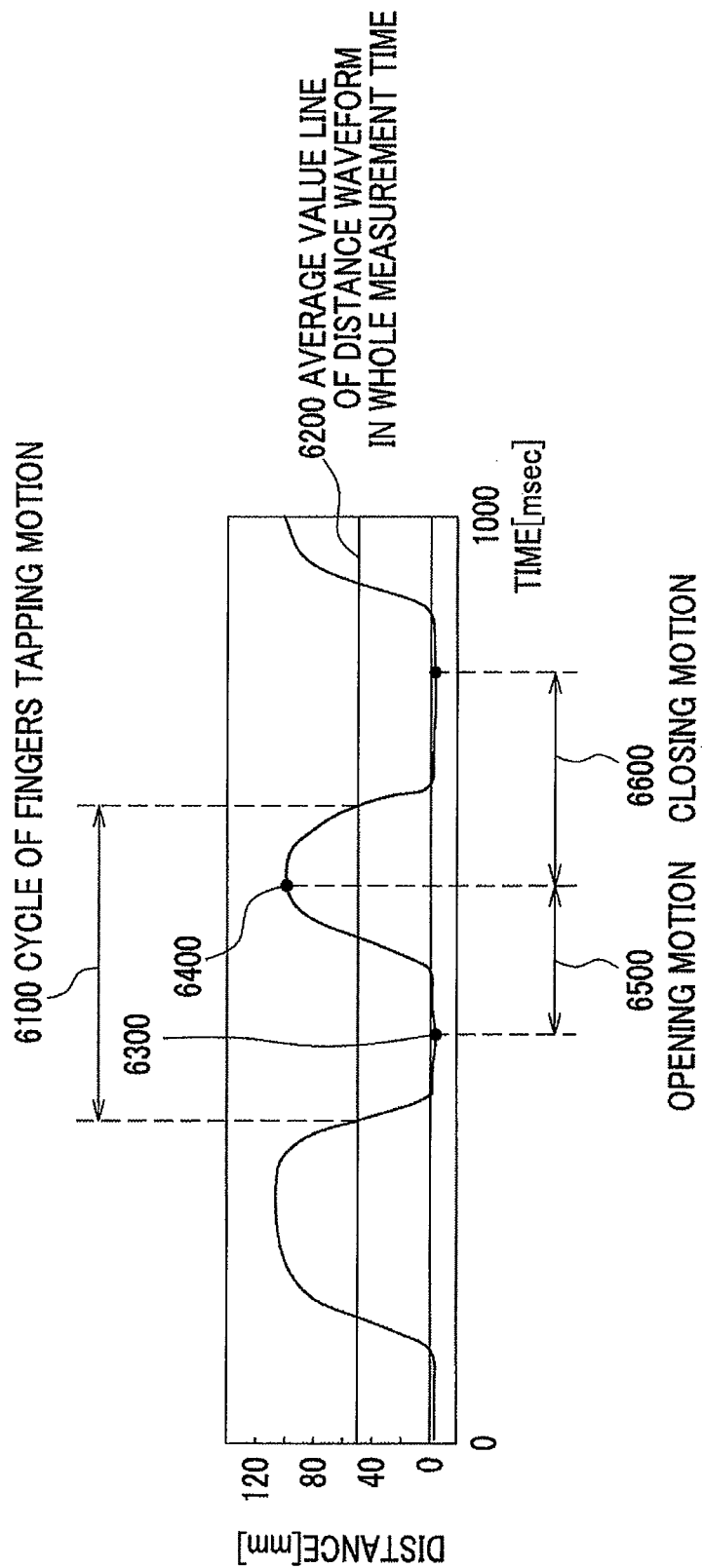

FIG.11

SUBJECT PERSON INFORMATION SETTING SCREEN IMAGE

PLEASE SET SUBJECT PERSON INFORMATION

SUBJECT PERSON ID _____ 11100

FULL NAME _____ 11200

BIRTH DATE _____ 11300

SEX ● Male ○ Female

DOMINANT HAND ● Right hand ○ Left hand ○ Both hands ○ Unknown 11400

MEMO _____ 11500

SAVE 11600

FIG.12

MEASUREMENT INFORMATION SETTING SCREEN IMAGE

SUBJECT PERSON INFORMATION

- SUBJECT PERSON ID
- FULL NAME
- BIRTH DATE
- SEX: ● Male ○ Female
- DOMINANT HAND: ● Right hand ○ Left hand ○ Both hands ○ Unknown
- MEMO

MEASUREMENT TIME

MEASUREMENT METHOD: ● Right hand ○ Left hand
○ Both Hands (simultaneously) ○ Both Hands (anti-phase)

COMMENT

CALIBRATION EXECUTION — 12400
MEASUREMENT START — 12500
CALIBRATION NOT — 12600
CLOSE

12100 — MEASUREMENT TIME
12200 — MEASUREMENT METHOD
12300 — COMMENT

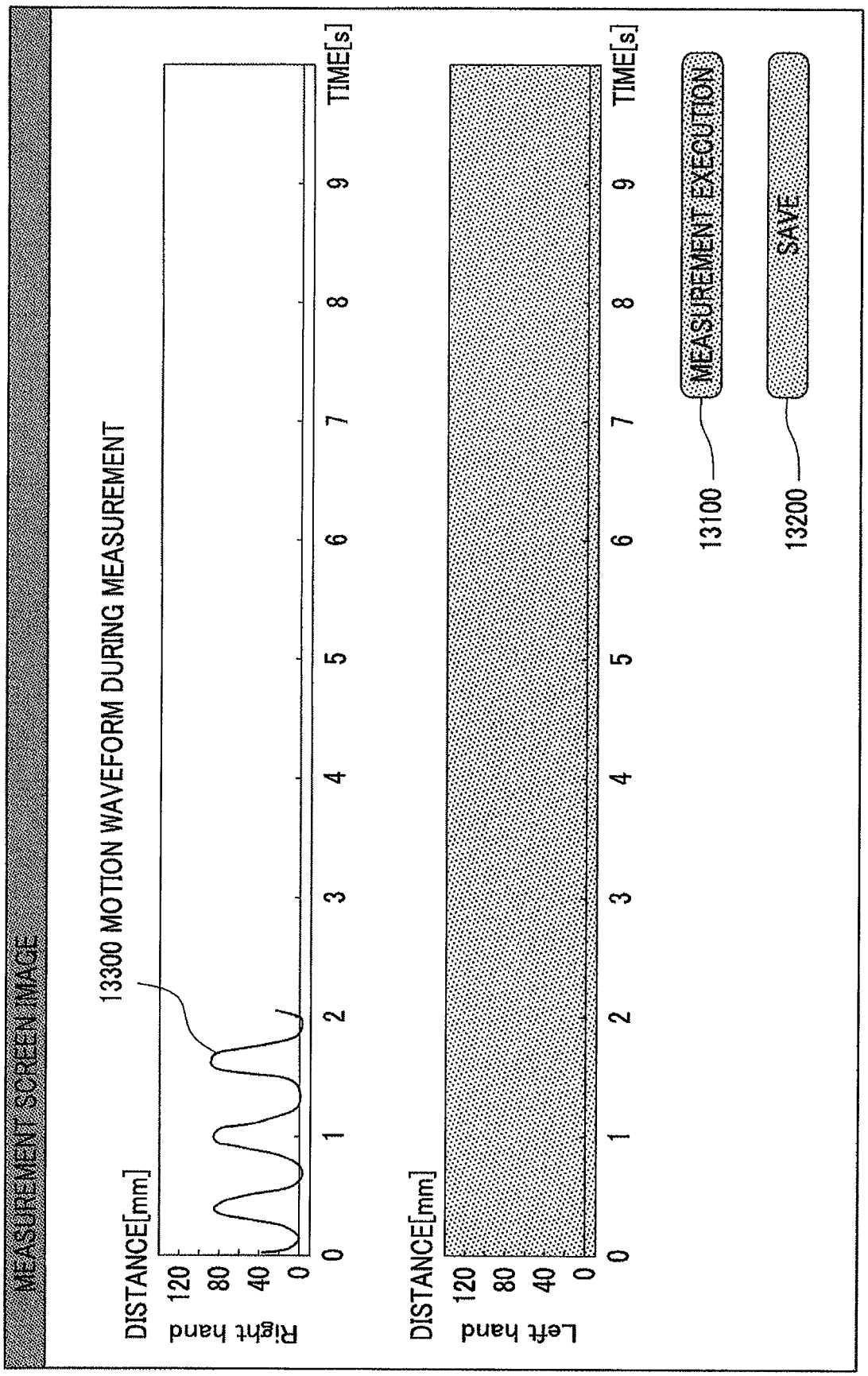

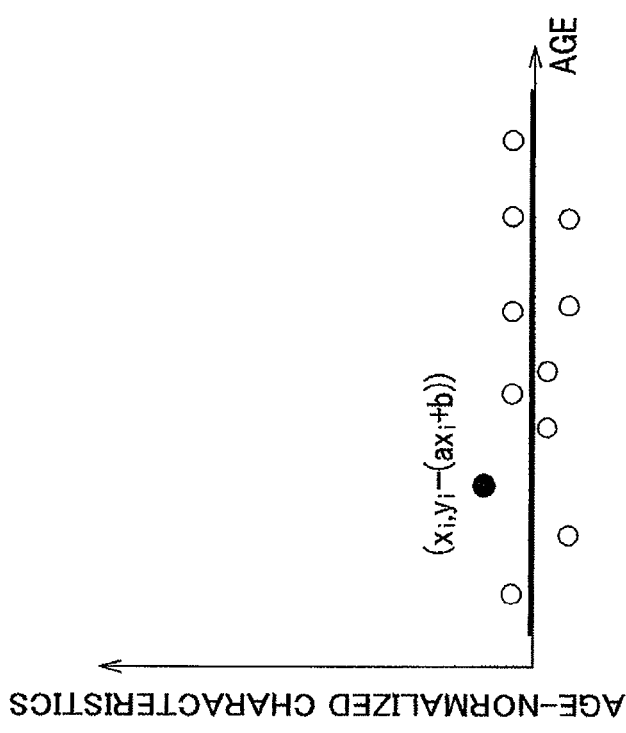
FIG.15A UN-NORMALIZED CHARACTERISTICS
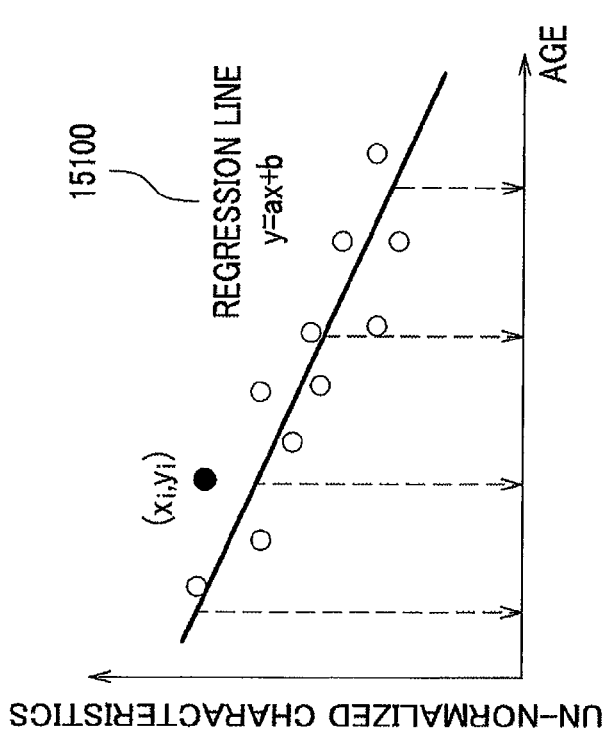
FIG.15B AGE-NORMALIZED CHARACTERISTICS

FIG.16

CHARACTERISTICS CORRESPONDING TO SYMPTOM OF PD

| SYMPTOM OF PD | CORRESPONDING CHARACTERISTICS |
|---|---|
| (i)TREMOR | THE NUMBER OF ZERO CROSSING TIMES ON SPEED WAVEFORM 5023 |
| | THE NUMBER OF ZERO CROSSING TIMES ON ACCELERATION WAVEFORM 5024 |
| (ii)RIGIDITY | AVERAGE OF MAXIMUM VALUES DURING OPENING MOTION ON ACCELERATION WAVEFORM 5015 |
| | AVERAGE OF MINIMUM VALUES DURING OPENING MOTION ON ACCELERATION WAVEFORM 5016 |
| | AVERAGE OF MAXIMUM VALUES DURING CLOSING MOTION ON ACCELERATION WAVEFORM 5017 |
| | AVERAGE OF MINIMUM VALUES DURING CLOSING MOTION ON ACCELERATION WAVEFORM 5018 |
| (iii)AKINESIA | AVERAGE OF LOCAL MAXIMUM VALUES ON DISTANCE WAVEFORM 5004 |
| | THE NUMBER OF TAPPING TIMES 5019 |
| | TOTAL MOTION DISTANCE ON DISTANCE WAVEFORM 5002 |
| | TOTAL ENERGY VALUE OF SPEED WAVEFORM 5013 |
| (vi)ABILITY FOR RHYTHM GENERATION | STANDARD DEVIATION OF TAPPING INTERVALS 5022 |
| | LOCAL STANDARD DEVIATION OF TAPPING INTERVALS 5026 |

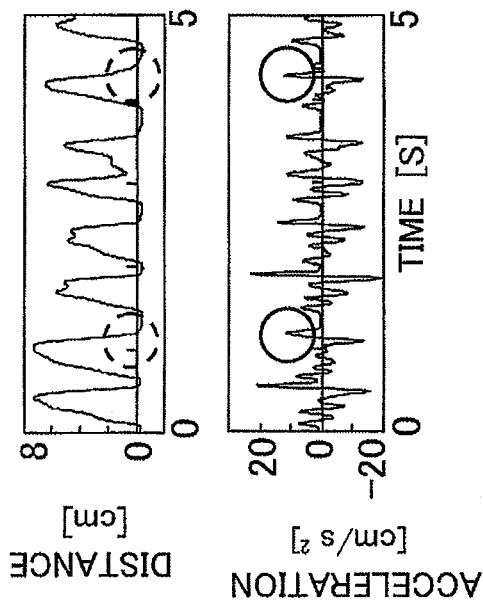
FIG. 17A THE NUMBER OF ZERO CROSSING TIMES ON ACCELERATION WAVEFORM 5024
FIG. 17B AVERAGE OF MAXIMUM VALUES DURING CLOSING MOTION ON ACCELERATION WAVEFORM 5017
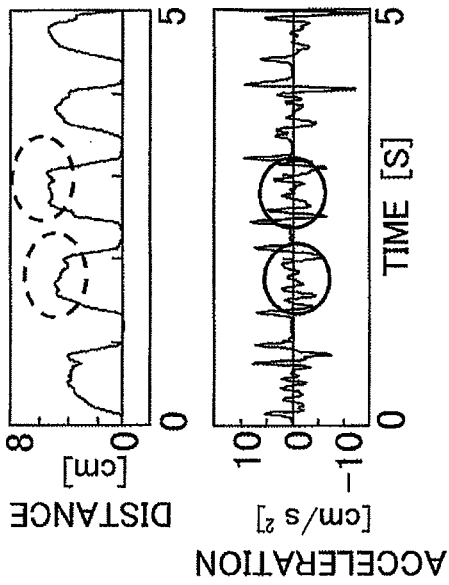
FIG. 17C AVERAGE OF LOCAL MAXIMUM VALUES ON DISTANCE WAVEFORM 5004
FIG. 17D STANDARD DEVIATION OF TAPPING INTERVALS 5022
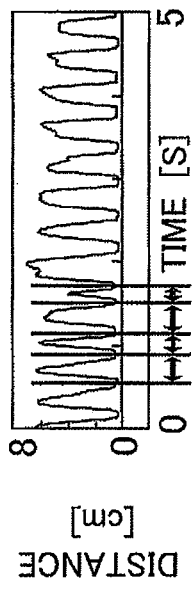
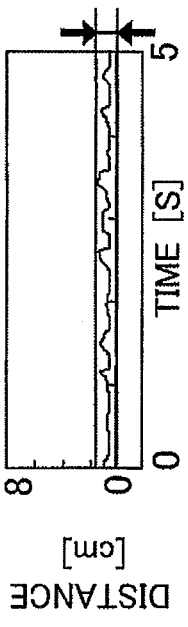

RELATION OF UPRDS AND MOTION DISORDER SYNTHESIS VALUE

FIG.19

ESTIMATION GROUP FOR FINGERS TAPPING MOTION

| NAME OF GROUP | THE TOTAL NUMBER | MALE | FEMALE | AGE | REQUIREMENT |
|---|---|---|---|---|---|
| HEALTHY PERSON GROUP(A) | 196 | 154 | 42 | 58.8±6.4 | — |
| HEALTHY PERSON GROUP(B) | 21 | 20 | 1 | 70.6±1.6 | HIGH AGE PERSONS OF HEALTHY PERSON GROUP(A) |
| MOTION DISORDER PERSON GROUP(A) | 23 | 10 | 13 | 70.3±6.4 | UPDRS≧1 |
| MOTION DISORDER PERSON GROUP(B) | 14 | 7 | 7 | 66.1±4.6 | UPDRS≧1, LOW AGE PERSONS OF MOTION DISORDER PERSON GROUP(A) |
| MOTION DISORDER PERSON GROUP(C) | 28 | 11 | 17 | 69.9±6.7 | UPDRS≧0 |

RELATION OF UPRDS AND MOTION DISORDER SYNTHESIS VALUE

PATIENT OF PARKINSON'S DISEASE

HEALTHY PERSON

AVERAGE OF ACCELERATIONS (SPEED=0)

- AUC = 0.7167
- SENSITIVITY = 0.6957
- SPECIFICITY = 0.6939

AVERAGE OF ACCELERATIONS (SPEED=0) (AFTER STANDARDIZATION)

- AUC = 0.5679
- SENSITIVITY = 0.6522
- SPECIFICITY = 0.5561

AVERAGE OF DIFFERENCE DEGREES FROM LISSAJOUS FIGURE (HEALTHY PERSON)

- AUC = 0.6162
- SENSITIVITY = 0.6957
- SPECIFICITY = 0.5561

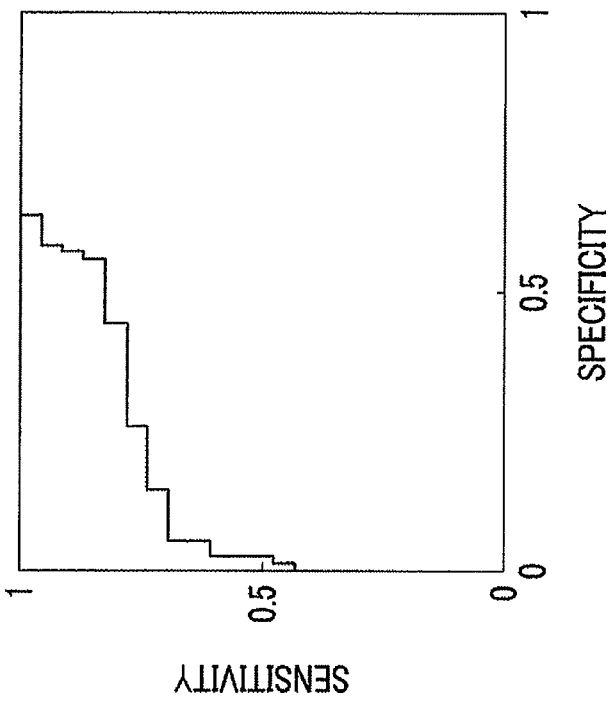
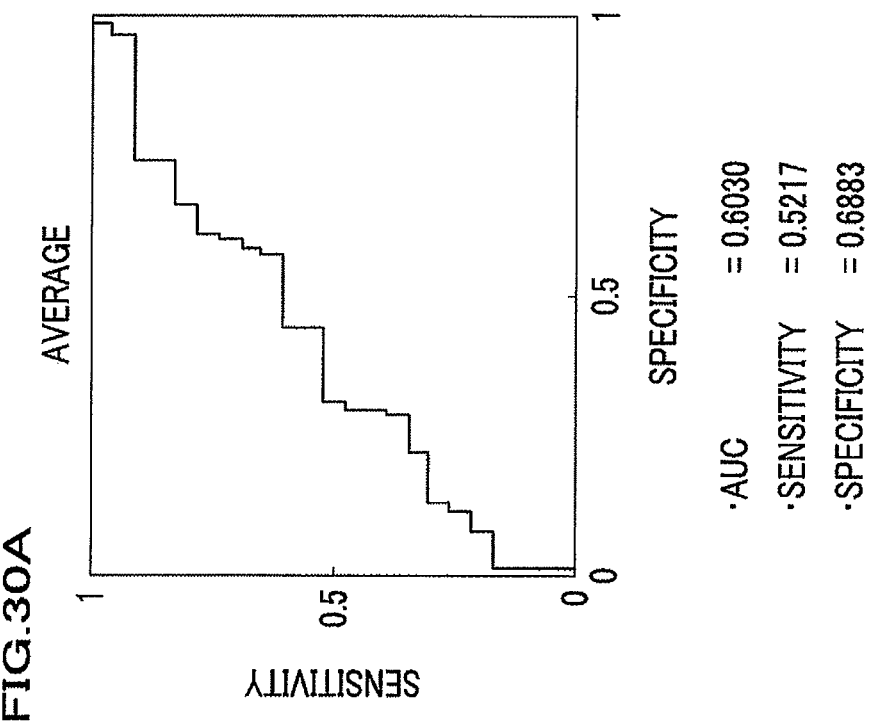
DISTANCE AT MAXIMUM OPENING SPEED

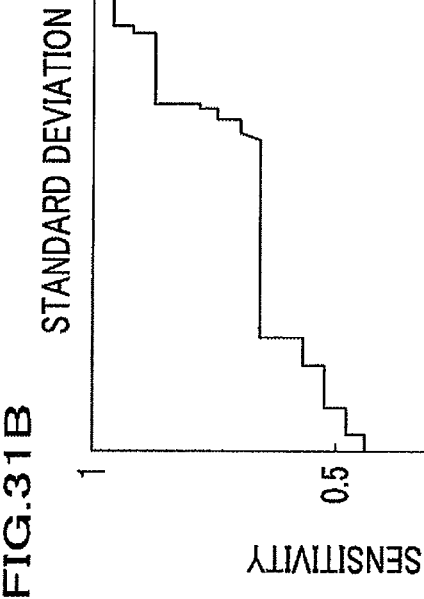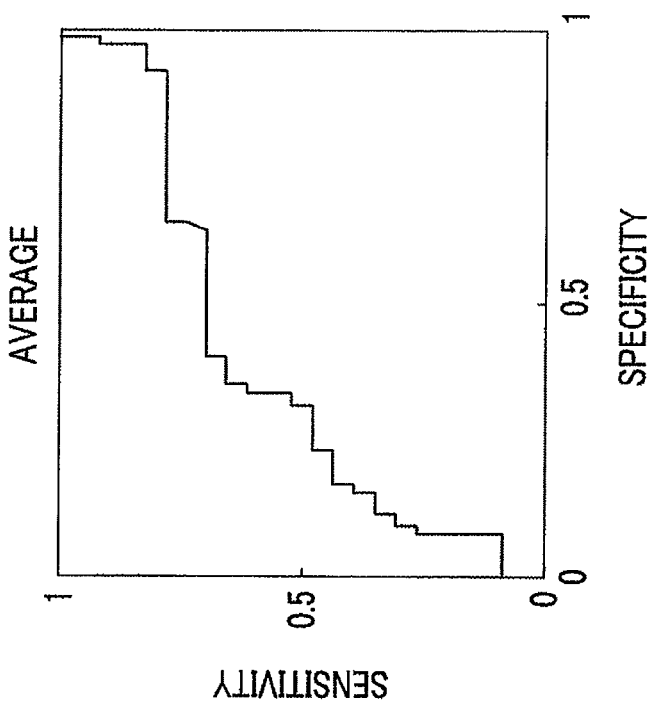

MOTOR FUNCTION ESTIMATING SYSTEM, MOTOR FUNCTION ESTIMATING METHOD AND PROGRAM

CLAIM OF PRIORITY

The present application claims priority from Japanese application JP 2009-196400A filed on Aug. 27, 2009, the content of which is hereby incorporated by reference into this application.

BACKGROUND OF THE INVENTION

1. Field of the Invention

The present invention relates to technology for estimating disease severity of motion disorder.

2. Description of the Related Art

In recent years, with the progress of the aging society, the number of patients having the motion disorder increases. The motion disorder is a disease in which a handicap of motor function happens. Examples of the motion disorder are Parkinson's disease, a cerebral apoplexy, cervical myelopathy, dementia, mental disease. For example, the Parkinson's disease that is a representative disease of the motion disorder is an intractable disease to bring a big obstacle for everyday life by trembling of hands and tightening of muscle and so on. There are about 145,000 patients of Parkinson's disease in Japan.

Conventionally, for a diagnosis method of the motion disorder, a method on which a doctor examines the patient by watching the motion of the patient and estimates the motion disorder by using score which shows disease severity is common. For, example, in the diagnosis of Parkinson's disease, UPDRS (Unified Parkinson's Disease Rating Scale) is used as an estimation standard (indicator) of the disease severity of Parkinson's disease widely. The doctor estimates the motor function by plural motions such as walk or fingers tapping motion (motion of a subject person repeatedly opening and closing a thumb and a forefinger of hand) with UPDRS.

But, so that the doctor performs a diagnosis and estimation with UPDRS subjectively, individual difference occurs between doctors. In other words the method with UPDRS is not objective. Technology to calculate an objective indicator for the disease severity of the motion disorder by the measurement and analysis of the fingers tapping motion is developed to solve this problem (refer to JP2005-152053A, JP2008-246126, "Kandori et al.," Quantitative magnetic detection of finger motions in patients with Parkinson's disease.", Neuroscience Research. Vol. 49, No. 2, 2004, pp 253-260"). For the objective indicator, characteristics calculated by waveform (distance waveform, speed waveform, acceleration waveform) of the fingers tapping motion is used, and the effectiveness as the objective indicator for the disease severity of Parkinson's disease is examined (M. Murata, et al, "Examination for the efficacy estimation of the finger tapping device to the patient of Parkinson's disease", The second motor function meeting for the study, 2007 Nov. 16, p 22)

But, it is often that the patient of the motion disorder develops various symptoms at the same time. About the Parkinson's disease, it is known that the plural symptoms such as four major signs (tremor, rigidity, akinesia, loss of postural reflex) develop at the same time. Therefore, it is difficult to estimate precisely disease severity of the motion disorder from characteristics which shows the degree of single symptom. In addition, it is often that the motion disorder develops in a senior person. Therefore there is a problem with a doctor making a subjective decision to be easy to mistake motor functional decline by the aging for the motion disorder.

This invention is intended to solve these problems. A purpose of this invention is to estimate disease severity of the motion disorder with high precision, by considering motor functional decline by the aging, and estimating plural symptoms of the motion disorder generally.

SUMMARY OF THE INVENTION

The present invention is a motor function estimating system comprising: a memory unit for storing waveform data with reference to time of fingers tapping motion; the waveform data is obtained by a motion sensor attached to a subject person who does the fingers tapping motion that is repetition of the opening and closing motion of two fingers of one hand; an analyzing section for analyzing the waveform data memorized in the memory unit; and a display unit for displaying an analysis result by the analyzing section; wherein the analyzing section comprises; a motion waveform generating section for making a motion waveform corresponding to the waveform data memorized in the memory unit; a characteristics generating section for making plural characteristics that represent feature of fingers tapping motion, based on the motion waveform; a motion disorder synthesis value generating section for creating motion disorder synthesis value that represents degree of motion disorder of the subject person by comparing the plural characteristics made by the characteristics generating section with corresponding characteristics on healthy persons previously stored in the memory unit and doing synthesizing the plural characteristics.

Thus, this invention can estimate disease severity of the motion disorder with high precision, by considering motor functional decline by the aging, and estimating plural symptoms of motion disorder generally.

BRIEF DESCRIPTION OF THE DRAWINGS

For a more complete understanding of the present invention and the advantages thereof, reference is now made to the following description taken in conjunction with the accompanying drawings wherein;

FIGS. 4A, 4B, 4C are the figure showing motion waveforms;

FIG. 5A is the list showing the kind of the characteristics to be calculated from the motion waveform;

FIG. 5B is the list showing the kind of the characteristics to be calculated from the motion waveform;

FIG. 6 is the figure for describing definition of the term of fingers tapping motion;

FIG. 11 shows an example of an input screen image of subject person information;

FIG. 12 shows an example of an input screen image of measurement data;

FIG. 13 shows an example of a measurement screen image which displays the motion waveform during measurement;

FIGS. 15A, 15B are the figure for describing calculation method of age-normalized characteristics;

FIG. 16 is the list showing characteristics corresponding to symptom of Parkinson's disease;

FIG. 17A-17D are the figure showing characteristics used when a motion disorder synthesis value about Parkinson's disease is calculated;

FIG. 19 is the list showing healthy person group and motion disorder person group that are estimation groups;

FIG. 27A is the figure showing relation sensitivity and specificity about average of acceleration (speed=0), FIG. 27B is the figure showing relation sensitivity and specificity about average (after a normalization) of acceleration (speed=0), FIG. 27C is the figure showing relation sensitivity and specificity about average of difference degree from Lissajous figure (healthy person);

FIGS. 30A, 30B are the figures about the distance at the maximum opening speed, FIG. 30A is the figure showing relation sensitivity and specificity about average, FIG. 30B is the figure showing relation sensitivity and specificity about standard deviation;

FIGS. 31A, 31B is the figure about the distance at the minimum closing speed, FIG. 31A is the figure showing relation sensitivity and specificity about average, FIG. 31B is the figure showing relation sensitivity and specificity about standard deviation.

DETAILED DESCRIPTION OF THE INVENTION

With reference to the drawings will be described embodiments of the invention in detail below.

This invention is applied to all kinds of the disease (Parkinson's disease, cerebral apoplexy, cervical myelopathy, dementia, mental disease and so on) that develops the motion disorder. In this embodiment, an application example of this invention to the Parkinson's disease will be described. In addition, this invention is applied to the various motions (walking, motion of hand or finger, motion of throat at the time of the deglutition, motion of mouth at the time of the pronunciation and so on) which the motion disorder affects. In this embodiment, an application example of this invention to the fingers tapping motion will be described.

(First Embodiment)

[Total Constitution]

Figure 1:
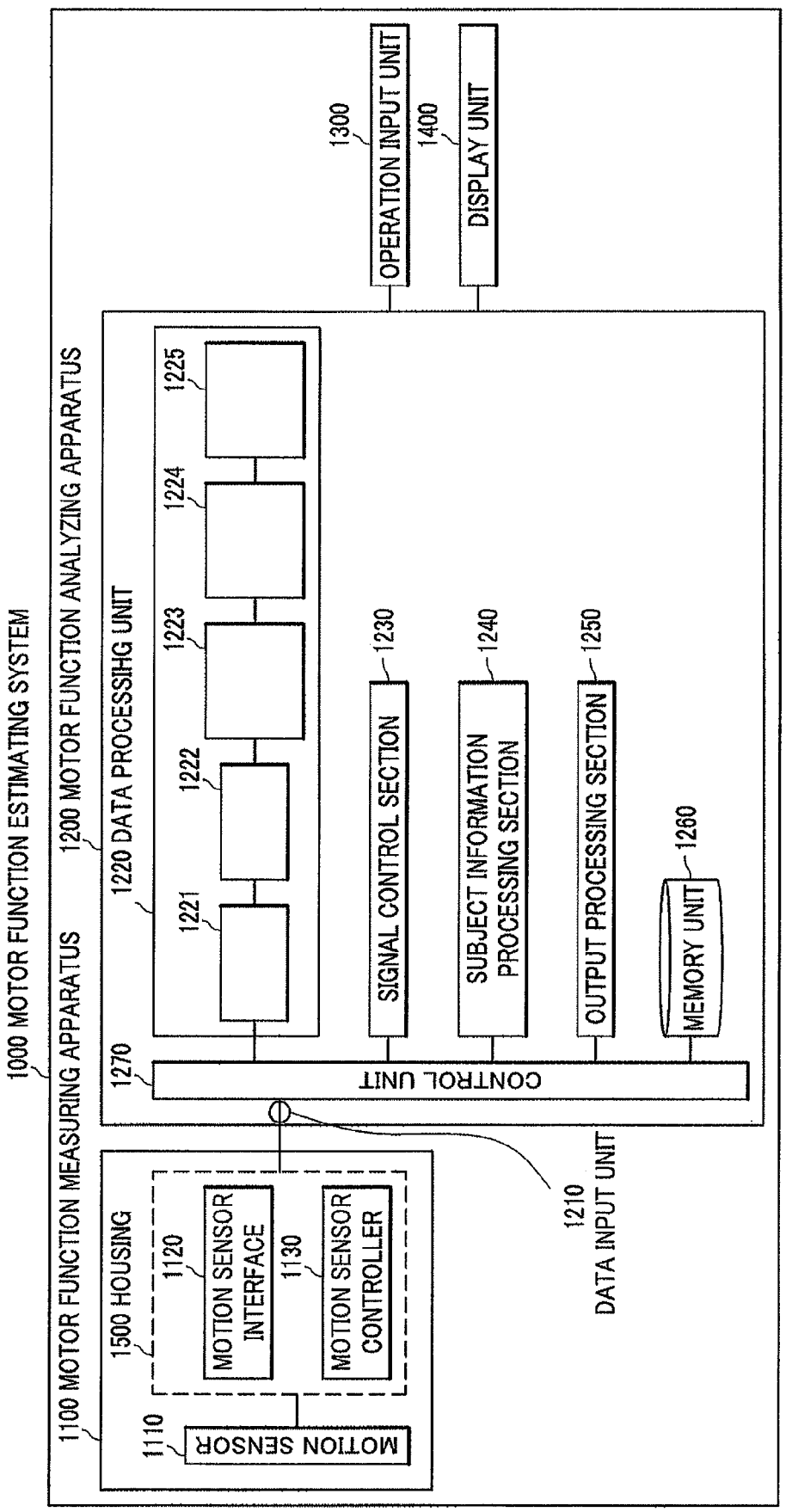
FIG. 1 is a block diagram showing the entire configuration of a motor function estimating system according to the embodiment.

As shown in FIG. 1, the motor function estimating system 1000 comprises a motor function measuring apparatus 1100 for measuring fingers motion of a subject person, a motor function analyzing apparatus 1200 for memorizing and analyzing data measured by the motor function measuring apparatus 1100, an operation input unit 1300 for being used to input the information of the subject person, a display unit 1400 for displaying measurement result and analysis result.

In this embodiment, the subject person is a measurement object by the motor function measuring apparatus 1100, and is a person who hopes inspection of affection or disease severity about Parkinson's disease. The motor function measuring apparatus 1100 measures the motion of the fingers of the subject person who does fingers tapping motion. The fingers tapping motion is the motion of the subject person repeatedly opening and closing a thumb and a forefinger of a hand as possible fast and large.

[Motor Function Measuring Apparatus]

The motor function measuring apparatus 1100 detects information of the fingers tapping motion of the subject person (motion information) with progress of time. The motor function measuring apparatus 1100 acquires the motion information (at least one of distance, speed, acceleration and jerk) of the subject person in form of waveform data.

The motor function measuring apparatus 1100 comprises a motion sensor 1110, a motion sensor interface 1120, and a motion sensor controller 1130. The motion sensor interface 1120 and the motion sensor controller 1130 are accommodated in only a housing 1500. In addition, the motion sensor interface 1120 and the motion sensor controller 1130 need not be accommodated in one housing.

[Motion Sensor]

Figure 2:
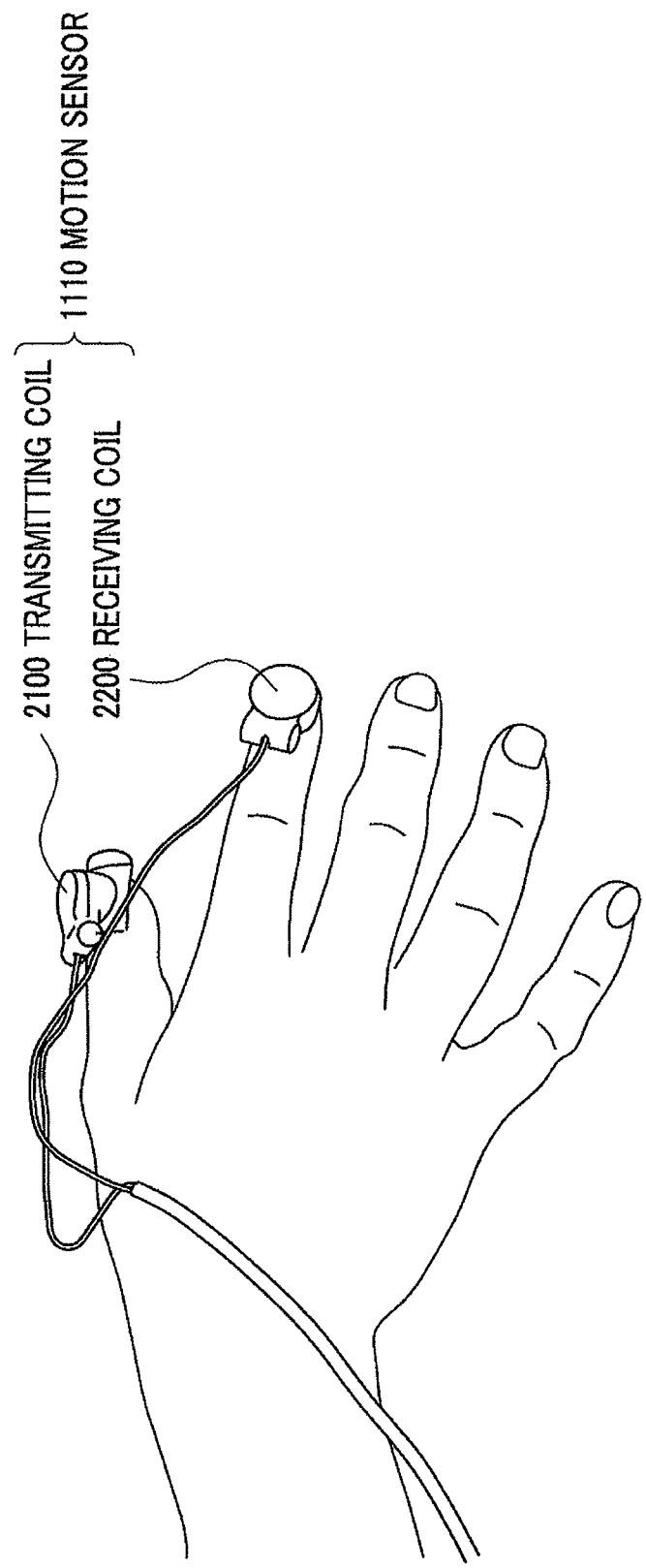
FIG. 2 is the figure showing a motion sensor attached to a hand.

As shown in FIG. 2, the motion sensor 1110 comprises a transmitting coil 2100 for generating a magnetic field (magnetic field generating section), a receiving coil 2200 for receiving the magnetic field (magnetic field receiving section).

For example, the transmitting coil 2100 is attached to a nail of the thumb by two sides adhesive tape. For example, the receiving coil 2200 is attached to a nail of the first finger by two sides tape. In addition, the transmitting coil 2100 may be attached to the nail of the first finger, the receiving coil 2200 may be attached to the nail of the thumb. In addition, the transmitting coil 2100 and the receiving coil 2200 may be attached to a part except the nail in the finger.

In addition, the transmitting coil 2100 and the receiving coil 2200 may be attached to a finger (for example, little finger) except the thumb and the first finger. In addition, the transmitting coil 2100 and the receiving coil 2200 may be attached to a part (for example, the palm near to the finger) except the finger. Therefore, the transmitting coil 2100 and the receiving coil 2200 may be attached to nail, finger and the palm of the subject person.

[Motion Sensor Interface]

The motion sensor interface 1120 includes an analog/digital conversion circuit. The motion sensor interface 1120 converts the waveform data of an analog signal detected by the motion sensor 1110 into the waveform data of the digital code with predetermined sampling frequency. The converted digital code is input into the motion sensor controller 1130.

[Motion Sensor Controller]

It will be described how the motion sensor controller 1130 acquires waveform data as follows.

Figure 3:
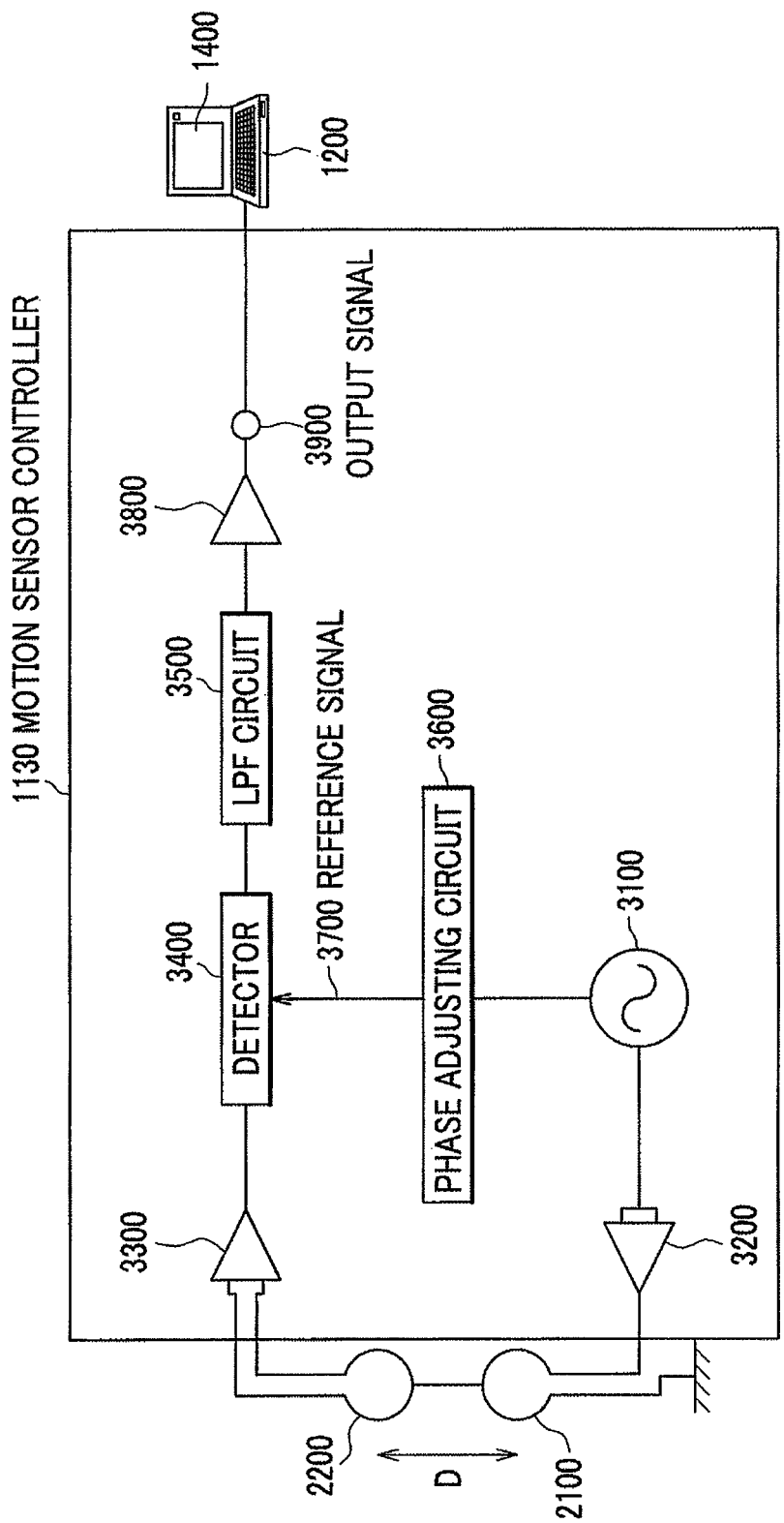
FIG. 3 is a block diagram showing the configuration of a motion sensor controller.

As shown in FIG. 3 (the motion sensor interface 1120 is not shown), an alternating current generating circuit 3100 (alternating current supplier) generates an AC voltage of a specific frequency (e.g., 20 kHz). The AC voltage of the specific frequency is converted by a current generating amplifier 3200 into an alternating current of the specific frequency, which is made to flow into the transmitting coil 2100. The magnetic field generated by the alternating current which flows in the transmitting coil 2100 induces an electromotive force in the receiving coil 2200.

The alternating current generated in the receiving coil 2200 by induced electromotive force (of the same frequency as the AC voltage of the specific frequency generated by the alternating current generating circuit 3100) is amplified by a preamplifier 3300, and the amplified signal is inputted to a detector 3400. The detector 3400 detects the amplified signal at the specific frequency generated by the alternating current generating circuit 3100 or at a frequency twice the specific frequency. Hence, a phase of the output of the alternating current generating circuit 3100 is adjusted by a phase adjusting circuit 3600, and the adjusted output inputted as a reference signal 3700 to a reference signal input terminal of the detector 3400.

The output signal of the detector 3400 passes through an LPF (Low-Pass Filter) circuit 3500 and is amplified by an amplifier 3800 to obtain a desired voltage and inputted to the motor function analyzing apparatus 1200. The output signal 3900 of the amplifier 3800 shows a voltage corresponding to the distance D between the receiving coil 2200 and the transmitting coil 2100 attached to the thumb and the first finger respectively. The detector 3400, the LPF circuit 3500, and the amplifier 3800 function as detected signal processing unit respectively. Although the case where the motion sensor 1110 is a magnetic sensor has been described above, an accelerometer, strain indicator and a high-speed camera instead of the motion sensor 1110 may be used.

[Motor Function Analyzing Apparatus]

As shown in FIG. 1, the motor function analyzing apparatus 1200 memorizes and analyzes data obtained by the motor function measuring apparatus 1100. The motor function analyzing apparatus 1200 comprises a data input unit 1210 for receiving output signal from the motion sensor controller 1130, a data processing unit 1220 for analyzing the output signal, a signal control section 1230 for transmitting measurement start signal to the motor function measuring apparatus 1100, a subject person information processing section 1240, an output processing section 1250 for processing analyzing result by the data processing unit 1220 in form to output it to the display unit 1400, the memory unit 1260 for storing data of the data processing unit 1220 and the subject person information processing section 1240, a control unit 1270 for controlling transmission/reception and processing of data

[Data Processing Unit]

The data processing unit 1220 calculates motion waveform of the fingers tapping motion of the subject person by using the output signal which the data processing unit 1220 received from the data input unit 1210 via the control unit 1270, and calculates an objective indicator which shows the disease severity of Parkinson's disease.

The data processing unit 1220 comprises a motion waveform generating section 1221, a characteristics generating section 1222, an age-normalized characteristics generating section 1223, a motion disorder synthesis value generating section 1224 and a motion disorder score estimating section 1225. In addition, the age-normalized characteristics generating section 1223 reduces an influence of the motor functional decline by the aging when the data processing unit 1220 estimates the decline of the motion function by the disease. Therefore, the age-normalized characteristics generating section 1223 is unnecessary when such a reduction is not necessary.

[Motion waveform generating section]

The motion waveform generating section 1221 converts an output signal (waveform data of the voltage) which the motion waveform generating section 1221 received from the motor function measuring apparatus 1100 into motion waveform equivalent. In addition, the motion waveform generating section 1221 generates distance waveform, speed waveform and acceleration waveform by differentiating/integrating the converted motion waveform by time.

For example, the conversion equation to convert the voltage into motion waveform (relative distance) is given, as follows. At first the calibration block that plural blocks of the different length (For example, 20, 30, 60 mm) are unified is prepared. The data set of voltage and the distance to be provided when two fingers grip each part of the plural length (20, 30, 60 mm) is made by the calibration block being used. And an approximation curve to minimize an error with the data set is provided as the conversion equation.

As shown in FIGS. 4A, 4B, 4C, distance waveform 4100 is obtained by converting the voltage with conversion equation. Speed waveform 4200 is obtained by differentiating the distance waveform 4100 by time. Acceleration waveform 4300 is obtained by differentiating the speed waveform 4200 by time. In addition, even if a strain gauge and an accelerometer are used for the motor function measuring apparatus 1100, "motion waveform" includes at least one of distance waveform, speed waveform, acceleration waveform and jerk waveform, as far as there is not limitation in particular. In addition, other motion waveforms (distance waveform, speed waveform, acceleration waveform, jerk waveform) are provided by differentiating/integrating if at least one motion waveform is measured.

[Characteristics Generating Section]

The characteristics generating section 1222 creates characteristics of the motion waveform obtained by the motion waveform generating section 1221. Characteristics 5023-5028 will be described in detail after it is described the term, as follows. In addition, detailed explanation is omitted about characteristics 5001-5022, because they are just what shown in FIGS. 5A and 5B.

As shown in FIG. 6, time from a time point when the distance becomes an average value line of the distance in whole measurement time 6200 and speed is smaller than 0 to a time point when the distance becomes the same condition next is defined as a cycle of fingers tapping motion 6100 (tapping interval). The point where the distance becomes smallest in one cycle is defined as a local minimum point 6300 of the distance waveform, and the distance at that time is defined as a local minimum value. Likewise, the point that the distance becomes biggest in one cycle is defined as a local maximum point 6400 of the distance waveform, and the distance at that time is defined as a local maximum value. The motion from a local minimum point to the next local maximum point of the distance waveform is defined as opening motion 6500. The motion from a local maximum point to the next local minimum value of the distance waveform is defined as closing motion 6600.

The number of zero crossing times on speed waveform 5023 (characteristics 5023) is value obtained by subtracting the number of tapping times 5019 from the number of times for which speed value turns to minus from plus in whole measurement time. In addition, the number of times for which speed value turns to plus from minus may be used instead of the number of times for which speed value turns to minus from plus.

Figure 7B:
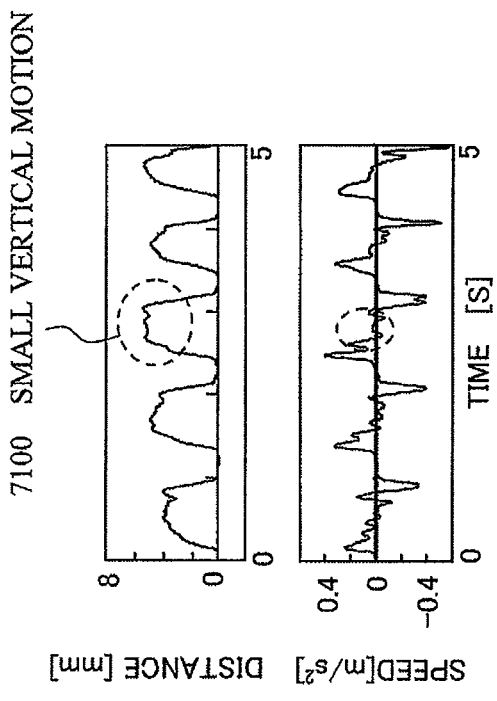
FIG. 7B is the figure for describing the number of zero crossing times of acceleration waveform.
Figure 7A:
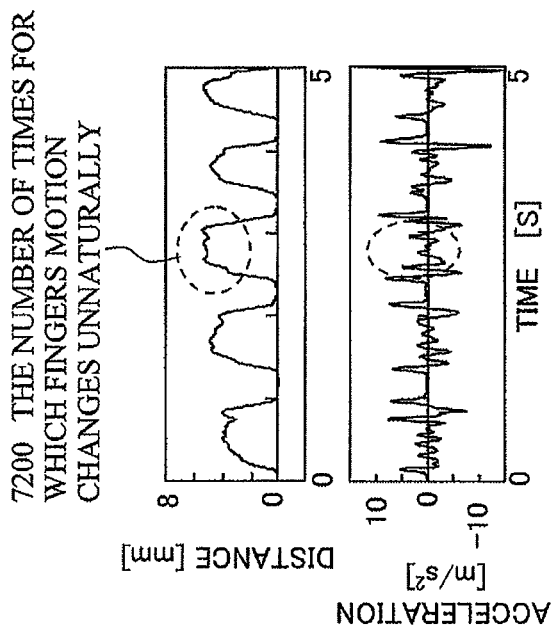
FIG. 7A is the figure for describing the number of zero crossing times of speed waveform.

As shown in FIG. 7A, the number of zero crossing times on speed waveform 5023 is a characteristics to count the number of small vertical motion small vertical motion 7100 except the big vertical motion of the fingers tapping motion that appears in distance waveform. The number of times for which speed waveform intersects zero corresponds to the number of times of small vertical motions of the distance waveform. It is thought that this characteristics is effective for estimation of the tremor (fine trembling) that represents the one of the symptoms of Parkinson's disease.

Likewise, the number of zero crossing times on acceleration waveform 5024 is the value obtained by subtracting the number of tapping times 5019 from the number of times for which acceleration value turns to minus from plus in whole measurement time. In addition, the number of times for which acceleration value turns to plus from minus may be used instead of the number of times for which acceleration value turns to minus from plus.

As shown in FIG. 7B, the number of zero crossing times on acceleration waveform 5024 is characteristics to count the number of times for, which fingers motion changes unnaturally 7200 including a fine vertical motion in the middle of fingers tapping motion. The number of times for, which acceleration waveform intersects zero corresponds to the number of times for which fingers motion changes unnaturally in the distance waveform. Like characteristics 5023, it is thought that this characteristics is effective for estimation of the tremor (fine trembling) that represents the one of the symptoms of Parkinson's disease.

Figure 8:
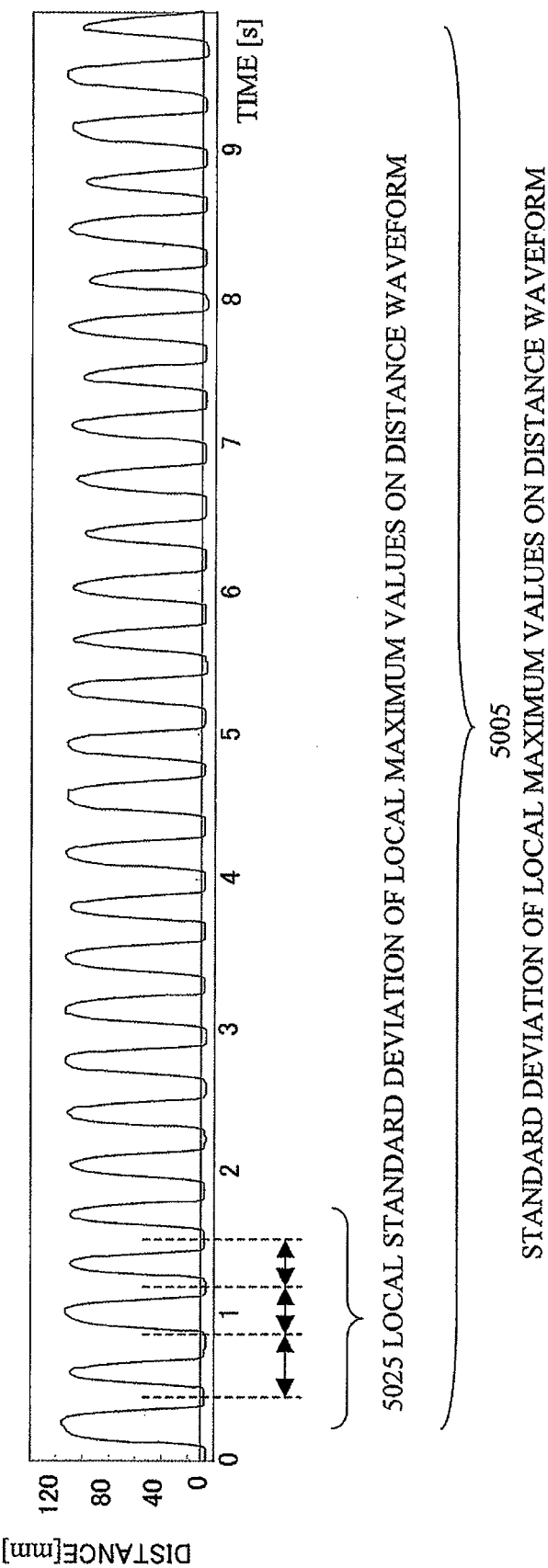
FIG. 8 is the figure for describing local standard deviation of amplitudes of distance waveform.

As shown in FIG. 8, local standard deviation of local maximum values on distance waveform 5025 is average of standard deviations of n local maximum values in a row on distance waveform in whole measurement time. In addition, "n" is an integer more than 2 and smaller than the number of tapping times. Local standard deviation of tapping intervals 5026 is average of standard deviations of n tapping intervals in a row in whole measurement time. In addition, "n" is an integer more than 2 and smaller than the number of tapping times.

About the person developing the motion disorder such as the Parkinson's disease, it is thought that a variation of the local amplitude is big for whole measurement time. On the other hand, about the healthy person, it is thought that there are not big variations of the local amplitude, but the amplitude shrinks for fatigue slowly for whole measurement time. Standard deviation of local maximum values on distance waveform 5005 is the value of standard deviation of local maximum values of distance waveform in whole measurement time. Therefore, it is difficult to distinguish a difference of both by standard deviation of local maximum values on distance waveform 5005. On the other hand, local standard deviation of local maximum values on distance waveform 5025 is the value calculated about a variation of the local amplitude continuously for whole measurement time. Therefore, it is thought that a difference of both can be distinguished by local standard deviation of local maximum values on distance waveform 5025. Likewise, it is thought that a difference of both can be distinguished by local standard deviation of tapping intervals 5026.

Figure 9:
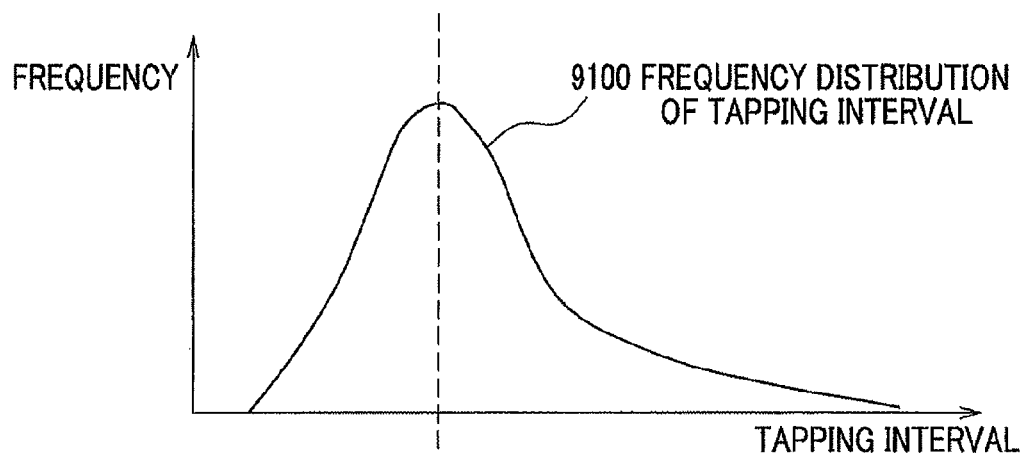
FIG. 9 is the figure for describing distortion degree of distribution of tapping intervals.

As shown in FIG. 9, distortion degree of distribution of tapping intervals 5027 is distortion degree of frequency distribution of tapping interval 9100 in whole measurement time. The distortion degree is a statistical indicator to show non-symmetricalness of the distribution, and, for example, is a value obtained by dividing the average of the cube of the deviations by the cube of the standard deviations.

It is thought that the frequency distribution of the tapping intervals of the healthy person becomes a form that is almost normal distribution. On the other hand, some long tapping intervals may get mixed with the frequency distribution of the tapping intervals of the person who develops the motion disorder such as the Parkinson's disease. Therefore it is thought that the frequency distribution becomes the shape. that a hem of the right direction of FIG. 9 spreads. Distortion degree of distribution of tapping intervals 5027 can show this property. In other words, it is thought that this distortion degree becomes almost "0" in the case of the frequency distribution of the healthy person, and this distortion degree becomes the comparatively big value in the case of the frequency distribution of the patient of Parkinson's disease.

Figure 10:
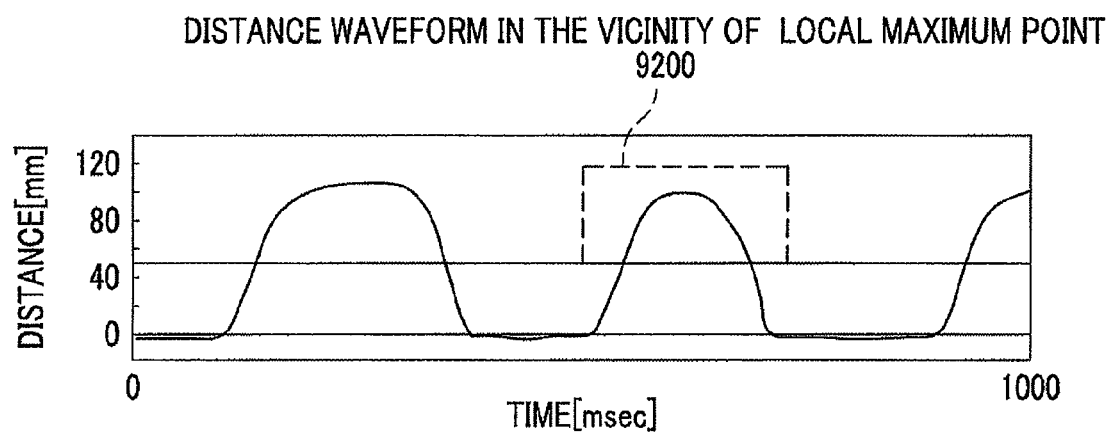
FIG. 10 is the figure for describing kurtosis of local maximum point of distance waveform.

Kurtosis of local maximum point 5028 is average of kurtosises of local maximum points of distance waveform in whole measurement time. The kurtosis is a statistical indicator to show sharpening degree of the distribution, and, for example, is a value obtained by dividing the average of the biquadratic of the deviations by the biquadratic of the standard deviations. As shown in FIG. 10, distance waveforms more than a constant value are extracted for distance waveform in the vicinity of local maximum point 9200. About the distance waveform in the vicinity of local maximum point 9200, kurtosis is calculated. It is thought that rigidity (the tightening of the muscle) which is a symptom observed in the person who develops the motion disorder such as the Parkinson's disease by kurtosis of local maximum point 5028 can be distinguished. The person who develops rigidity cannot change opening motion and the closing motion of two fingers smoothly. It is thought that distance waveform in the vicinity of local maximum point is sharp so that the change is suddenly performed.

Characteristics 5001-5028 shown in FIGS. 5A and 5B are named un-normalized characteristics (that does not be age-normalized) as follows. In addition, another statistical indicator (for example, variance) to show the unevenness of data may be used instead of standard deviation when un-normalized characteristics is calculated. In addition, un-normalized characteristics may be standardized by distance when two fingers are opened in a maximum so that the data of the persons that sizes of hands are different are treated equally.

[Age-Normalized Characteristics Generating Section]

The age-normalized characteristics generating section 1223 calculates age-normalized characteristics by revising un-normalized characteristics 5001-5028 generated by the characteristics generating section 1222 by age. To be concrete, at first the age-normalized characteristics generating section 1223 calculates age-normalized characteristics by substituting the age of the subject person memorized in the memory unit 1260 for an estimate equation described later. And the age-normalized characteristics generating section 1223 calculates age-normalized characteristics by subtracting age quantity of presumed characteristic from un-normalized characteristics. In addition, it will be described about a calculation method and the effect of the age-normalized characteristics later.

[Motion Disorder Synthesis Value Generating Section]

The motion disorder synthesis value generating section 1224 calculates motion disorder synthesis value (MDSV) by composing plural age-normalized characteristics with the following equation (1). In addition, it will be described later the details of the calculation method by the equation (1) and the effect of the MDSV.

[Motion Disorder Score Estimating Section]

The motion disorder score estimating section 1225 calculates motion disorder score by substituting MDSV for an approximation function which shows relations with MDSV and the score of the disease severity of the motion disorder. In addition, it will be described later about the calculation method of the approximation function and the effect of motion disorder score.

[Signal Control Section]

The signal control section 1230 transmits a measurement start signal to the motor function measuring apparatus 1100. When the motor function measuring apparatus 1100 does not receive a measurement start signal, the motor function measuring apparatus 1100 becomes the standby state. When the motor function measuring apparatus 1100 receives a measurement start signal, the motor function measuring apparatus 1100 becomes the measurable state.

[Subject Person Information Processing Section]

The subject person information processing section 1240 manages subject person information, the analysis result information and so on with subject DB (Data Base) in the memory unit 1260.

In other words, the subject person information processing section 1240 performs next four processing by cooperation with subject DB mainly.

1) Registration, revision, deletion, search and sort of the subject person information
2) Linkage with the subject person information and measurement data
3) Registration, revision, deletion of the analysis result of measurement data (addition, revision and deletion of the item)
4) When statistical processing is performed, registration, revision, deletion of the result of the statistical processing In addition, for example, the subject person information registered in subject DB is subject person ID, full name, the date of birth, age, height, weight, disease name, comment about the subject person. In addition, the management of these informations by the subject person information processing section 1240 is realized easily by well-known program and data constitution.

[Output Processing Section]

The output processing section 1250 displays the information such as subject person information registered in subject DB, the analysis result to the display unit 1400 in a form (for example, graph, table) that it is easy to be understood visually. In addition, the output processing section 1250 may display all analysis results in the display unit 1400 at the same time, or only an item appointed by a user in the display unit 1400.

[Control Unit]

The control unit 1270 comprises CPU (Central Processing Unit), ROM (Read Only Memory), RAM (Random Access Memory). Operation processing is carried out by program, data memorized in the memory unit 1260 being loaded to the control unit 1270. Hereby, the signal control section 1230, the subject person information processing section 1240 and the output processing section 1250 in the data processing unit 1220 are realized.

[Operation Input Unit]

The operation input unit 1300 is means for user of the motor function estimating system 1000 to input the subject person information. The operation input unit 1300 is realized by a keyboard and a mouse. In addition, as user interface used by a user to input the subject person information, an input screen may be displayed in the display unit 1400.

[Display Unit]

The display unit 1400 is means to output the subject person information and the motion information processed by the data processing unit 1220. For example, the display unit 1400 is realized by LCD (Liquid Crystal Display), CRT (Cathode Ray Tube) display, printer and so on.

(Screen Image Example)

As follows, it will be described screen image examples displayed in the display unit 1400 with reference to FIG. 11-FIG. 14.

As shown in FIG. 11, subject person information setting screen image comprises subject person ID input column 11100, full name input column 11200, birth date input column 1300, dominant hand input column 11400 and memo input column 11500. The user (for example, doctor) inputs each information into these input columns and clicks a save button 11600 by a mouse. Then the input the subject person information is stored in the memory unit 1260 by the subject person information processing section 1240. In addition, the age calculated by the date of birth is used for calculation by the age-normalized characteristics generating section 1223.

As shown in FIG. 12, measurement information setting screen image comprises measurement time input column 12100, measurement method input column 12200 and comment input column 12300. The user (for example, doctor) inputs measurement information into these input columns. And calibration is carried out when a user presses a calibration execution button 12400. When a user presses a measurement start button 12500, a measurement is started. The execution situation (use or nonuse) of the calibration is displayed in display column of execution situation of the calibration 12600. In addition, input of the measurement information and the execution of the calibration may be performed in order of reverse.

As shown in FIG. 13, in measurement screen image that displays motion waveform during measurement, when a user (for example, doctor) presses a measurement execution button 13100, the measurement is started, and motion waveform during measurement 13300 is displayed. When a user presses a save button 13200 after the end of the measurement, the motion waveform and the analysis result to be provided by the data processing unit 1220 are stored, and an analysis result output screen shown in FIG. 14 opens. In addition, motion waveform may be stored, analysis result may be not stored, and calculation by the data processing unit 1220 may be performed appropriately on this occasion.

Figure 14:
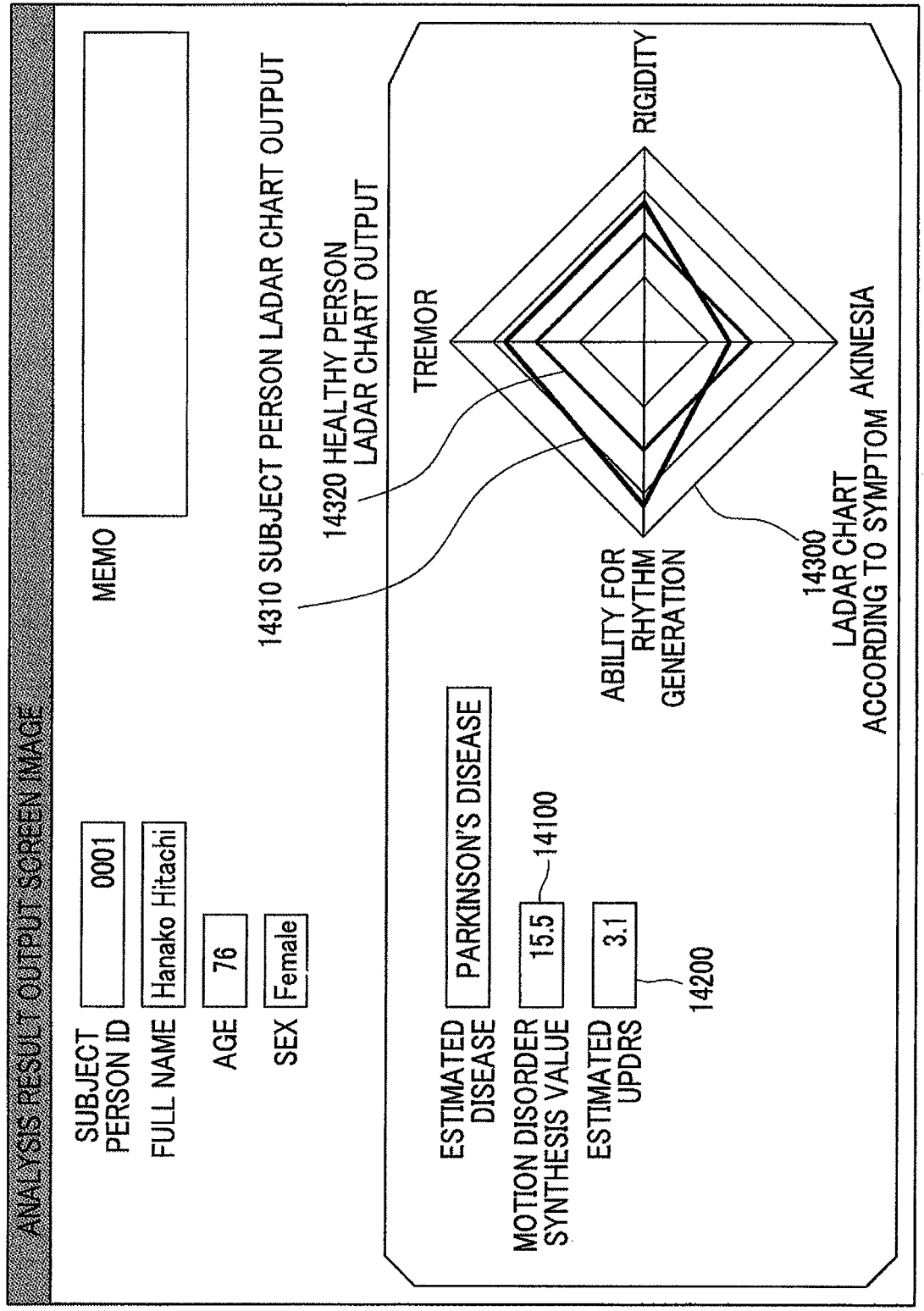
FIG. 14 shows an example of analysis result output screen image.

As shown in FIG. 14, in the analysis result output screen image which displays analysis result by the data processing unit 1220, MDSV calculated by the motion disorder synthesis value generating section 1224 is displayed in 14100, estimated UPDRS (motion disorder score) calculated by the motion disorder score estimating section 1225 is displayed in 14200 (motion disorder score output column). In addition, a value ($x_i$) to be provided by a calculation process of the MDSV is displayed in a ladar chart according to symptom 14300 as a value to show each symptom of Parkinson's disease. The doctor who watches the ladar chart according to symptom 14300 can distinguish easily which symptom is worse. In addition, subject person ladar chart output 14310 is displayed in a very thick line, and healthy person ladar chart output 14320 is displayed in thick line. By this, comparison with the subject person and the healthy person by the viewing becomes easy. In addition, it is not necessary for these all information to be displayed. In addition, by operation of the tab indication, the indication screen of the motion waveform and a screen displaying the numerical value of the characteristics may appear.

[Calculation Method of Age-Normalized Characteristics]

The characteristics generating section 1222 calculates plural un-normalized characteristics about healthy person group. It is preferable to have many data of the healthy person group. It is preferable for age of the healthy person group to agree with age of motion disorder person group that has high onset rate of motor disorder.

Next, as shown in FIG. 15A, about each un-normalized characteristics, regression line 15100 (age is a dependent variable. un-normalized characteristics is an independent variable.) is calculated. "○" and "●" are un-normalized characteristics in FIG. 15A. And, as shown in FIG. 15B, age-normalized characteristics is a value obtained by subtracting an estimate by the regression line from un-normalized characteristics. Calculated age-normalized characteristics is relative quantity compared with the mean every age, not absolute quantity. Therefore, when motor functional decline by the disease is estimated, influence of the motor functional decline by the aging decreases by the use of age-normalized characteristics.

In addition, age-normalized characteristics may be a value obtained by subtracting an estimate by the regression line from the value obtained by dividing un-normalized characteristics by standard deviation every age. In addition, instead of a regression line, the change of the characteristics by the aging may be calculated by other functions (a multinomial expression, an exponential function, a logarithmic function) and correspondence list of age and the characteristics being used. In addition, revision by the age is performed for all characteristics in this embodiment, but revision by the age needs not to be performed about the characteristics that has not significant difference by the age.

[Calculation Method of MDSV]

It will be described calculation method of the MDSV as follows. It is said that the Parkinson's disease is described by six symptoms. Six symptoms are four main symptoms ((i), (ii), (iii), (iv)) and (v) and (vi).

(i) tremor
(ii) rigidity
(iii) akinesia
(iv) loss of postural reflex
(v) decrease of the ability to perform two motion at the same time
(vi) decrease of the ability for rhythm generation It is thought that it is (i) (ii) (iii) (vi) to be strong in relations with the fingers tapping motion. In addition, the number of symptoms may be other numbers except four. In addition, the kind of the symptoms may be limited by a point of view of effective symptom to check effect of the medication.

Here, plural things corresponding to each symptom are chosen from age-normalized characteristics by criteria for selection of following (i) (ii) (iii) (vi) (corresponding to above (ii) (iii) (vi)). For example, this choice is performed by the judgment of the doctor (see FIG. 16). In addition, in FIG. 16, "PD" means "Parkinson's disease".

(i) Characteristics to show small motion except the big motion in fingers tapping motion
  (ii) Characteristics about the acceleration which may be connected with muscular strength
  (iii) Characteristics to show the degree of amplitude or the number of tapping times
  (vi) Characteristics to show unevenness of the rhythm And, about chosen age-normalized characteristics, performance to distinguish motion disorder group (patient of Parkinson's disease group) from healthy person group is estimated by AUC (Area Under The ROC Curve). About each symptom ((i) (ii) (iii) (vi)), characteristics of highest AUC is chosen one by one as $x_i$. AUC is an indicator for the performance to distinguish characteristics, is value calculated for an area under the ROC (Receiver Operating Characteristic) curve, and takes values of 0.5-1. If value of AUC is high, performance to distinguish is high (see FIGS. 30A, 30B, 31A and 31B).

In addition, as an estimation method of the performance to distinguish, statistical indicator such as F-number (the unbiased variance ratio), the Mahalanobis' distance may be used instead of AUC. In addition, instead of the choice of characteristics by statistical indicator, a doctor may choose characteristics.

For example, as $x_i$ (i=1, 2, 3, 4), four characteristics shown in the FIG. 17A-17D are chosen. As shown in FIG. 17A, the number of zero crossing times on acceleration waveform 5024 is the number of times for which acceleration waveform intersects zero (the number of a small vertical motion in the distance waveform that represents a feature of the tremor). By the number of zero crossing times on acceleration waveform 5024, tremor is estimated.

Likewise, as shown in FIG. 17B, by average of maximum values during closing motion on acceleration waveform 5017, the muscular strength at the moment when fingers are closed becomes clear, and rigidity is estimated. Likewise, as shown in FIG. 17C, by average of local maximum values on distance waveform 5004, size of the motion becomes clear, and akinesia is estimated. Likewise, as shown in FIG. 17D, by standard deviation of tapping intervals 5022, unevenness of the tapping interval becomes clear, and rhythm generation disorder is estimated.

And these age-normalized characteristics are composed by equation (1).

$$MD = \frac{1}{n}\sum_{i=1}^{n} x_i^* f_i \qquad \text{equation (1)}$$

$$x_i^* = \frac{x_i - \overline{x}_{i,n}}{\sigma(x_{i,n})}, \quad f_i = \{1, -1\}$$

In equation (1), $x_i$ (i=1, 2, ..., n) is age-normalized characteristics. $\overline{x}_{i,n}$ (In this specification, "−" is a sign attached on a letter just before it.) is the means of $x_i$ about the healthy person group. $\sigma(x_{i,n})$ is standard deviation of $x_i$ about the healthy person group. $x^*_i$ is the value obtained by normalizing $x_i$ by data of the healthy person group. In addition, $f_i$ is a value to coordinate a plus and minus so that a plus direction of $x_i$ shows disease severity. In other words, when average of $x_i$ about the motion disorder group is bigger than average of $x_i$ about the healthy person group, f=1 is used, and f=−1 is used in the case of the reverse. In addition, when $x_i$ are composed, the distinction score that is provided by distinction analysis being applied to $x_i$ may be used without equation (1) being used.

[The Calculation Method of the Approximation Function of MDSV and the UPDRS]

Figure 18:
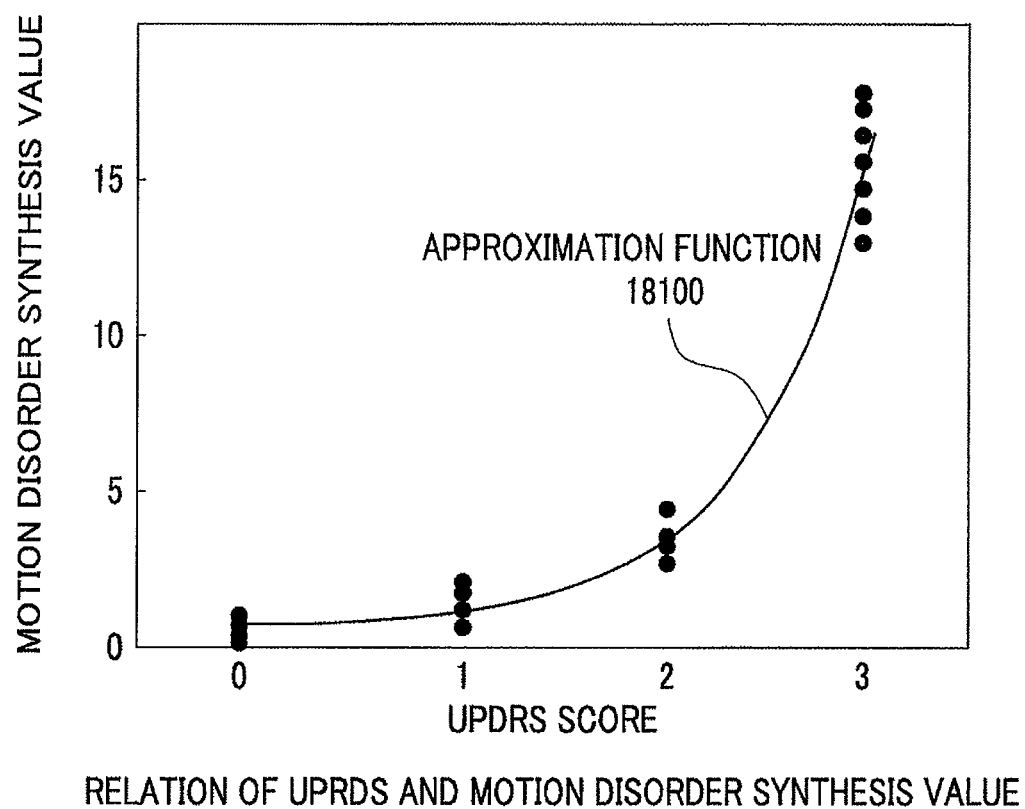
FIG. 18 is the figure showing relation of UPDRS and the motion disorder synthesis value.

By MDSV about the motion disorder group and UPDRS (score of the disease severity of Parkinson's disease) being used, an approximation function which shows relations of both is calculated. It is desirable that there are data of wide disease severity about motion disorder group so that the precision of the approximation increases. As shown in FIG. 18, at first, data set of UPDRS and the MDSV is plotted, Next, with the least-squares method, plot group is matched with a function (for example, linear function, quadratic function, exponential function). On this occasion, most suitable approximation function 18100 is decided by function and the each weight coefficient being decided.

[Effect by the Age-Normalized Characteristics]

Figure 20:
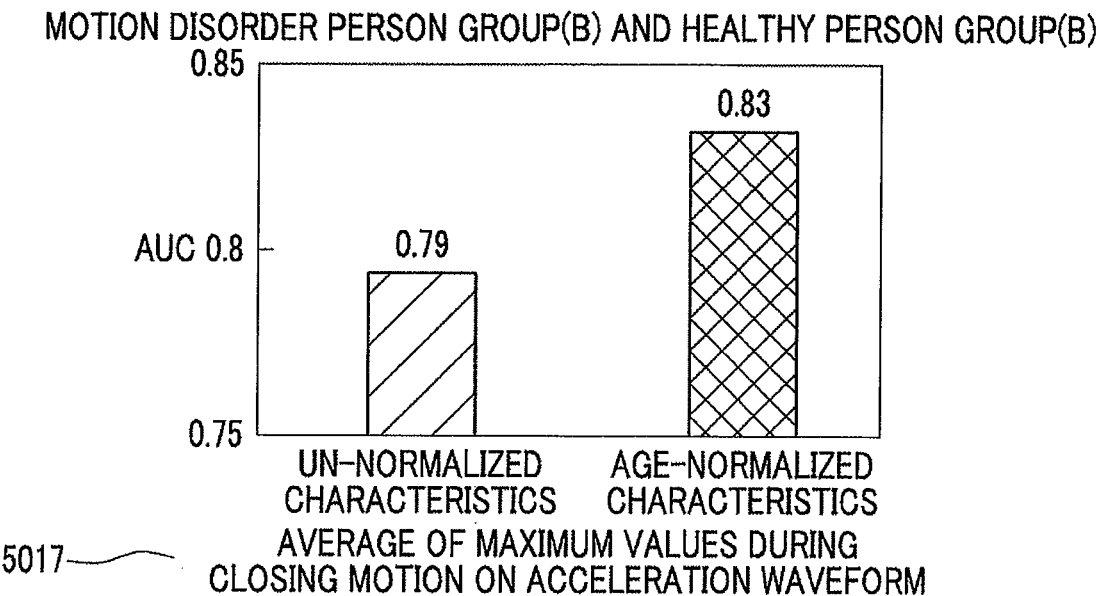
FIG. 20 is the figure showing identification performance of age-normalized characteristics.

FIG. 20 is a graph of the comparison of AUC of age-normalized characteristics and the un-normalized characteristics about characteristics 5017 at identification of motion disorder group (B) limited to the young group and the healthy person group limited to the class of advanced age (B) (see FIG. 19). Because AUC of the age-normalized characteristics is bigger than AUC of the un-normalized characteristics, it may be said that the performance to distinguish of the age-normalized characteristics is high. Likewise, about 26 of the 28 characteristics shown in FIG. 5A and FIG. 5B, AUC of the age-normalized characteristics is bigger than AUC of the un-normalized characteristics. Therefore, it may be said that the performance to distinguish of the age-normalized characteristics is higher than the performance to distinguish of the un-normalized characteristics.

[Effect of MDSV]

Figure 21:
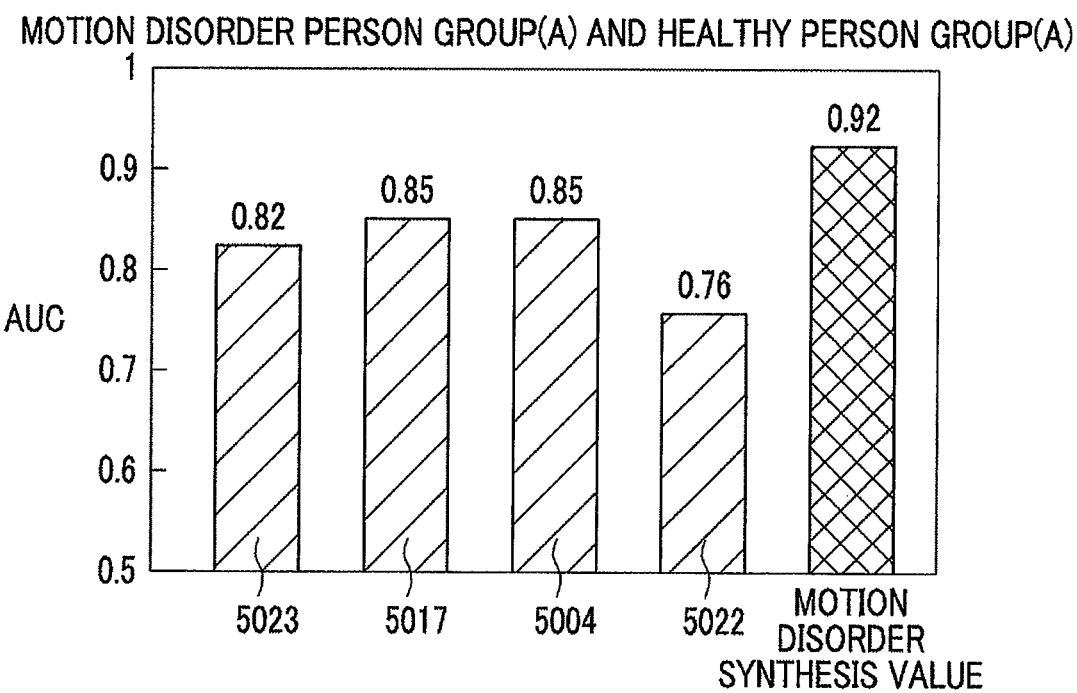
FIG. 21 is the figure showing identification performance of the motion disorder synthesis value.

FIG. 21 is a graph of the comparison of AUC of the characteristics chosen for characteristics corresponding to each symptom and AUC of the MDSV at identification of motion disorder group (A) and the healthy person group (B) (see FIG. 19). Because AUG of the MDSV is the highest, it may be said that the performance to distinguish of the MDSV is the highest.

Figure 22:
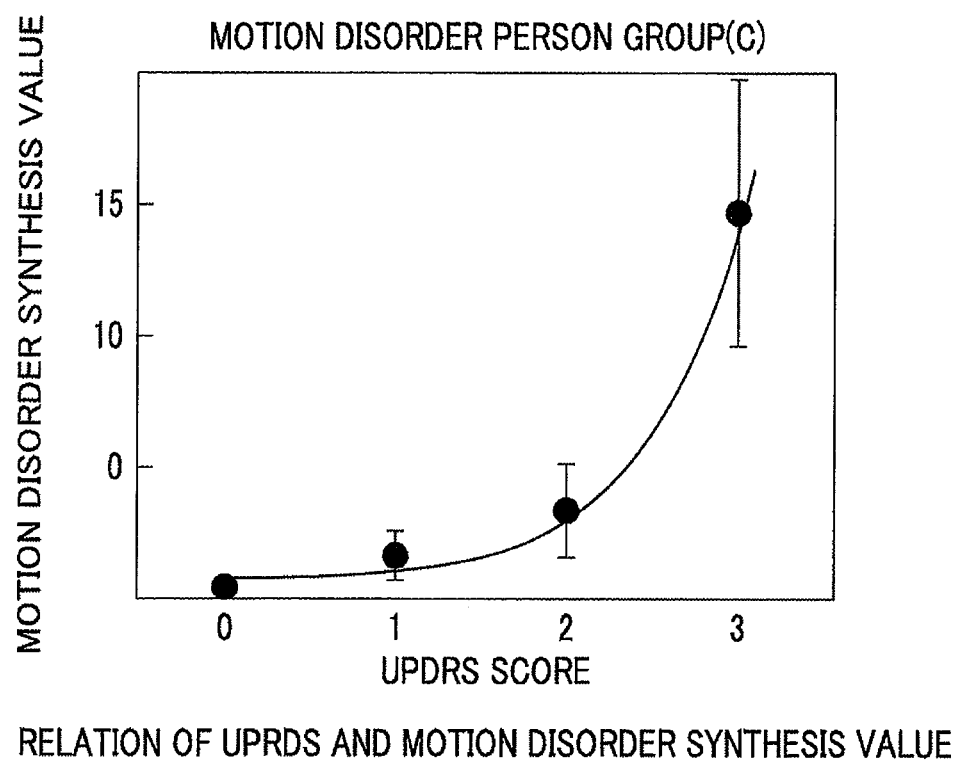
FIG. 22 is the figure showing relation of UPDRS and the motion disorder synthesis value.

FIG. 22 is a figure which shows the relations with score of the finger tapping of the UPDRS and the MDSV, about motion disorder group (C) shown in FIG. 19. A linear function, a quadratic function and an exponential function were done a fitting to the relations by the least-squares method. As a result, the exponential function was fitted the relations most, and the decision weight coefficient at that time was 0.77. Because agreement degree of MDSV and of the UPDRS is high, it may be said that the MDSV is effective for an indicator for the objectivity of the disease severity. In addition, the line extending to the top and bottom direction of "●" in FIG. 22 shows standard deviation.

[Effect]

According to the motor function estimating system 1000 of the first embodiment, the disease severity of Parkinson's disease is estimated with high precision, because the plural symptoms of Parkinson's disease are estimated generally by MDSV in comparison with the case that one symptom is estimated. In addition, it can be reduced influence of the motor functional decline by the aging, because age-normalized characteristics is used when MDSV is calculated.

(Second Embodiment)

With reference to the drawings will be described a second embodiment of the invention in detail below. In the second embodiment, an application example of this invention to the Parkinson's disease will be described, like the case of the first embodiment. In addition, because FIGS. 1-4, FIGS. 6-15B, FIG. 18, FIG. 19 are similar to the first embodiment, those explanations are omitted.

For the characteristics generated by the characteristics generating section 1222, contact time in the fingers tapping motion is calculated. The calculation method of this characteristics is described as follows.

In the second embodiment, contact time (time for which two fingers are in contact), and finger motion time (time for which two fingers move without contact) in the fingers tapping motion by the subject person are calculated. Contact time and finger motion time can be measured directly by a touch sensor. However, in the second embodiment, contact time and finger motion time are calculated with motion waveform of the fingers tapping motion.

Figure 23:
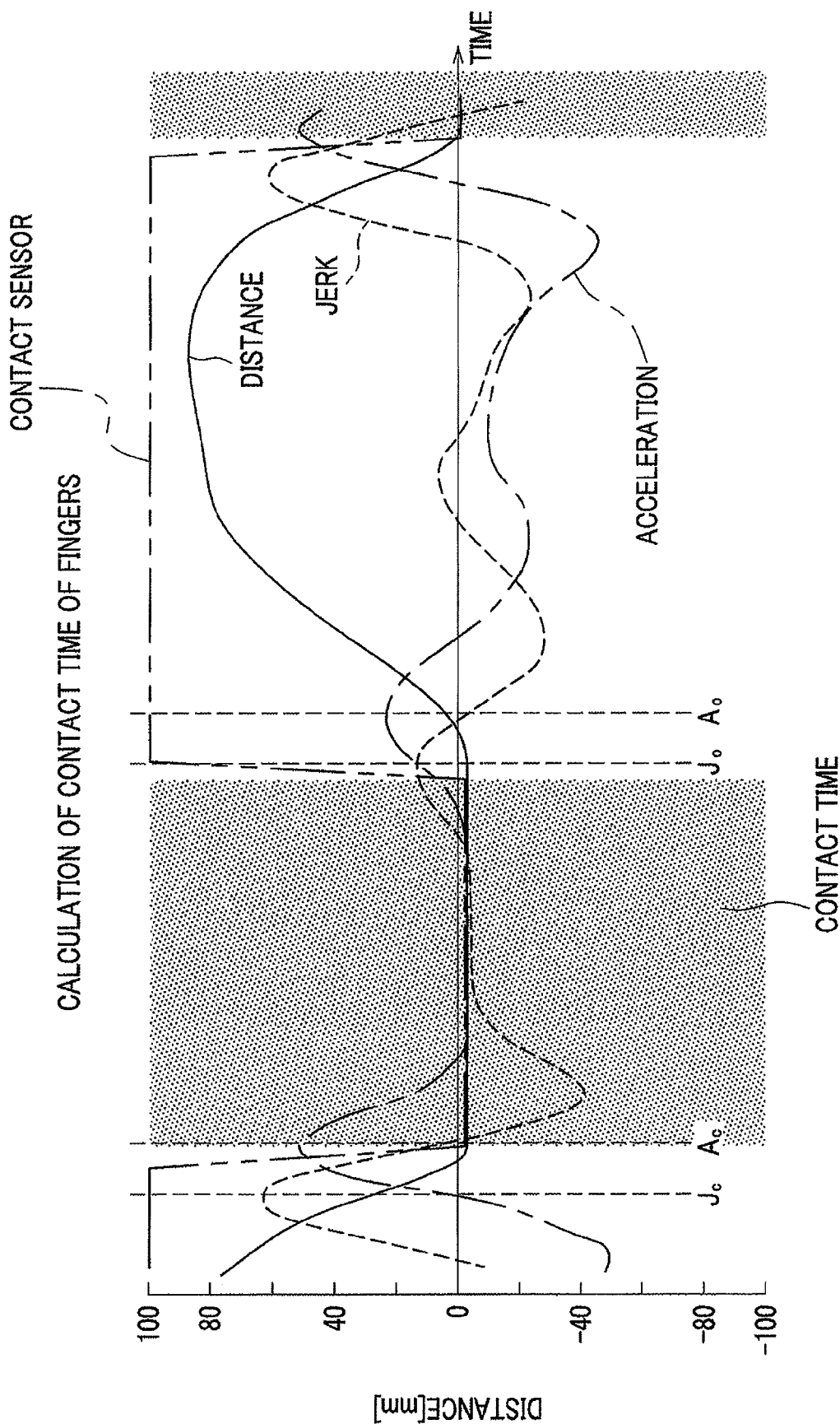
FIG. 23 is the figure for describing calculation of contact time of fingers.

In FIG. 23, relation with distance waveform, acceleration waveform and jerk waveform in the time of the fingers tapping motion by the subject person and the contact time of two fingers measured by a touch sensor are shown. In acceleration waveform, $A_C$ is the maximum value in the time of the closing motion, and $A_o$ is the maximum value in the time of the opening motion. In addition, in jerk waveform, $J_C$ is the maximum value in the time of the closing motion, and $J_o$ is the first maximum value in the time of the opening motion.

As shown in FIG. 23, the time of the $A_C$ and the start time of the contact time of two fingers are about the same. In addition, the time of the $J_o$ and the end time of the contact time of two fingers are about the same. In other words, the contact time of two fingers of the subject person can be calculated approximately precisely without a sensor such as the touch sensor by information being used at the time of $A_C$ and $J_o$. In addition, if the contact time of two fingers is calculated, finger motion time can be calculated by subtracting the contact time from one cycle of time of the fingers tapping motion.

The patient of Parkinson's disease has six symptoms described above. Therefore it is thought that the contact times of two fingers (finger motion time) are different between patient of Parkinson's disease and healthy person. Therefore, the contact time of two fingers can be used as one of the characteristics for calculation of MDSV.

(Third Embodiment)

With reference to the drawings will be described a third embodiment of the invention in detail below. In the third embodiment, an application example of this invention to the Parkinson's disease will be described, like the case of the first embodiment. In addition, because FIG. 1-4, FIG. 6-15B, FIG. 18, FIG. 19 are similar to the first embodiment, those explanation is omitted. In addition, in this embodiment, data of the fingers tapping motion by a subject person ordered to move a finger as possible wide and fast were used. However, the subject person may perform fingers tapping motion by the constant amplitude without opening two fingers in a maximum.

[Calculation Method of the Characteristics]

Figure 24A:
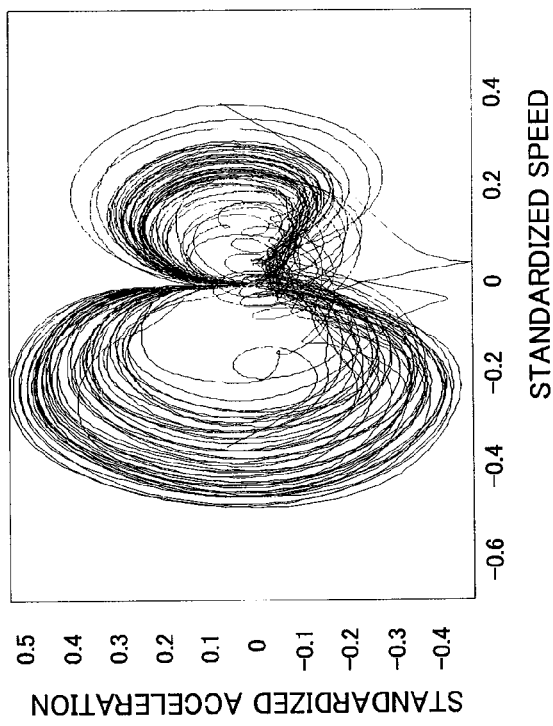
FIG. 24A is a Lissajous figure for healthy person.
Figure 24B:
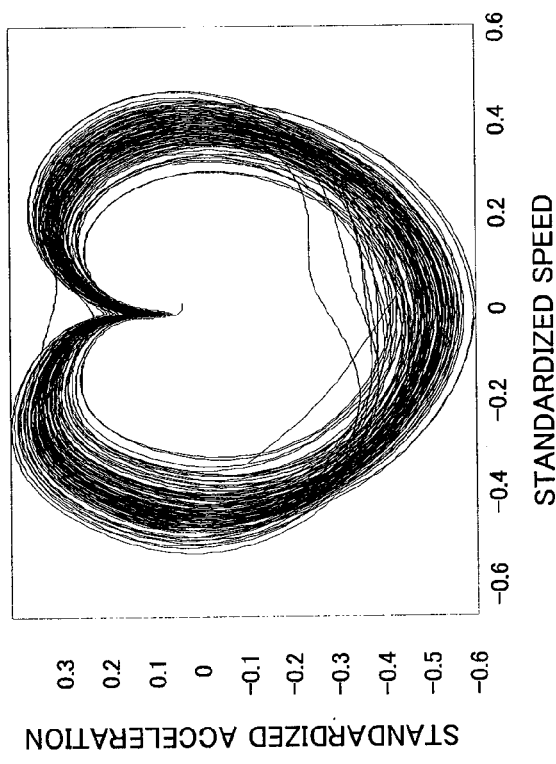
FIG. 24B is a Lissajous figure for patient of Parkinson's disease.

The characteristics generating section 1222 (see FIG. 1) calculates similarity of the shape of Lissajous figure shown in FIGS. 24A, 24B for characteristics. When a cross axle is speed of the fingers tapping motion, and a vertical axis is acceleration of the fingers tapping motion, the Lissajous figure is the figure which is provided by points in whole measurement time being plotted. In addition, acceleration and speed are standardized with each largest amplitude in Lissajous figure, so that individual difference of acceleration and speed are removed, and a difference of the shape becomes clear more, As shown in FIG. 24A, it is thought that the Lissajous figure for the healthy person tends to become the heart-shape. As shown in FIG. 24B, it is thought that the Lissajous figure for the patient of Parkinson's disease tends to become the gourd-shape. The reason is described as follows. At first, in the Lissajous figure for the healthy person, the part that both speed and acceleration become 0 (or almost 0) is one place (A point in time to switch over from closing motion to opening motion). On the other hand, in the Lissajous figure for the patient of Parkinson's disease, the parts that both speed and acceleration become 0 are two places (A point in time to switch over from closing motion to opening motion and a point in time to switch over from opening motion to closing motion).

In other words the healthy person can shift from opening motion to closing motion smoothly. However, in the case of patient of Parkinson's disease, motion stops once between opening motion and closing motion because of the tightening of the muscle.

Figure 25:
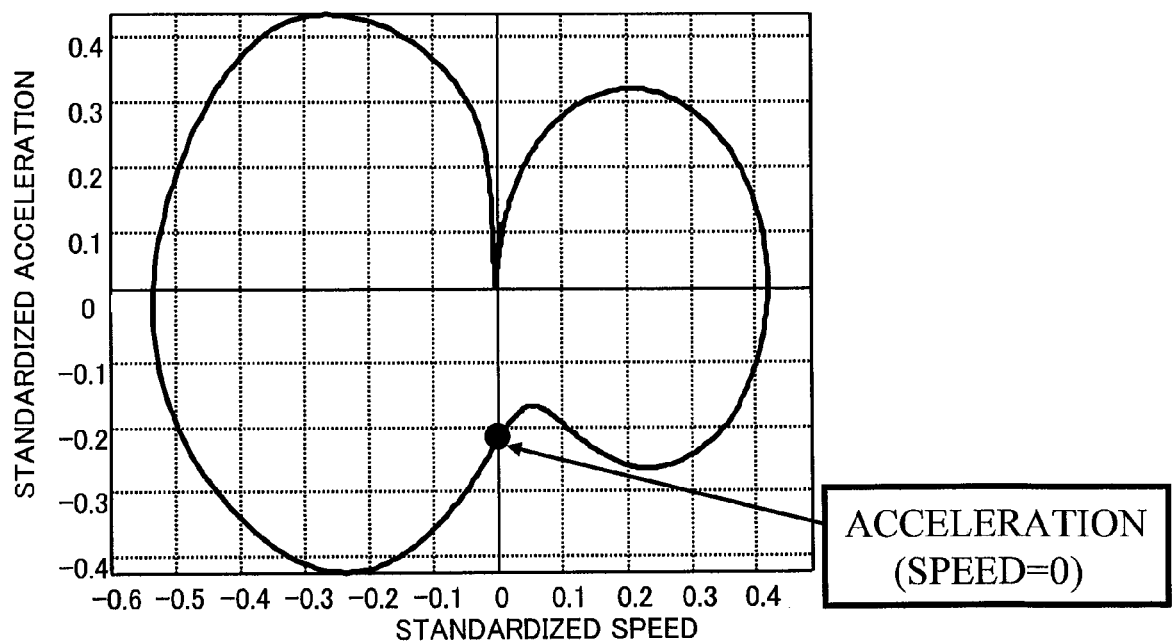
FIG. 25 is the figure for describing method of calculating characteristics from the Lissajous figure.

Similarity of the shape of the Lissajous figure is calculated to catch this feature. Concretely, for characteristics, acceleration in the vicinity of local maximum point of the Lissajous figure is calculated. As shown in FIG. 25, in Lissajous figure of the fingers tapping motion for one cycle, there are points of intersection with the vertical axis (speed=0). Among the accelerations of plural points of intersection, the minimum ("●" in FIG. 25) is chosen. For characteristics, average of this acceleration for whole measurement time is calculated.

Figure 26:
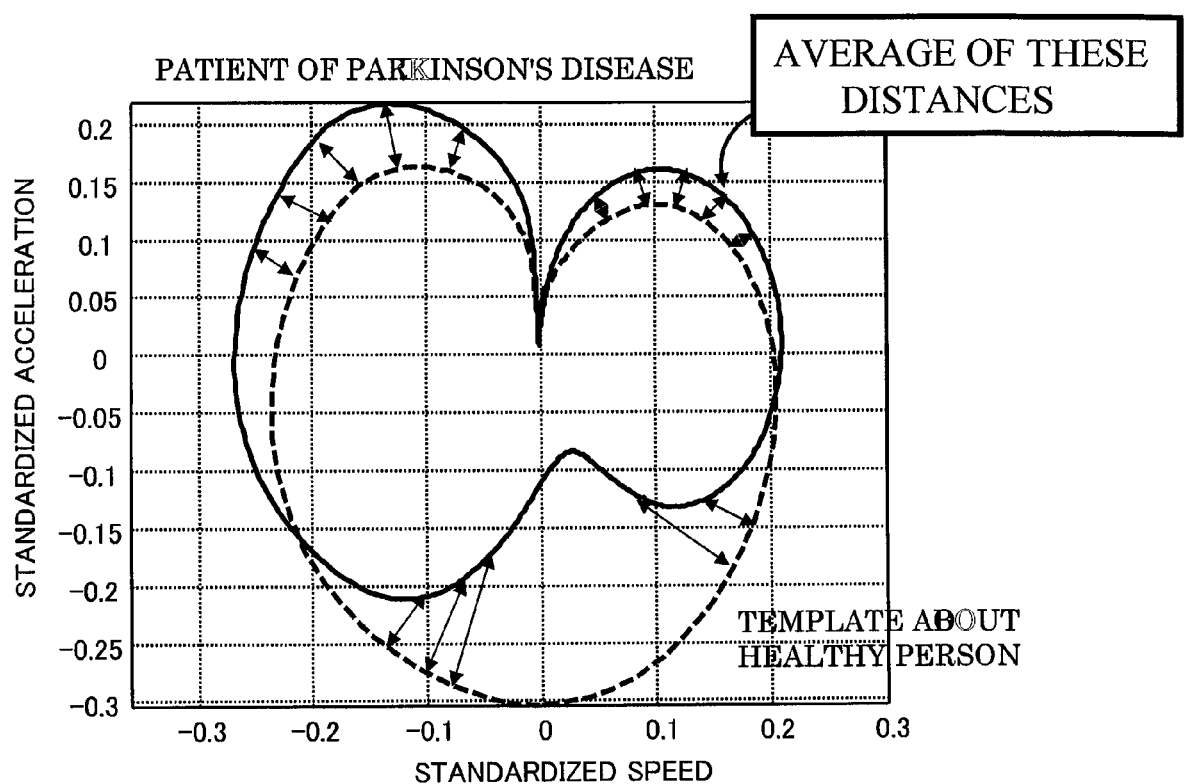
FIG. 26 is the figure for describing method of calculating characteristics from the Lissajous figure.

In addition, difference degree with shape of the Lissajous figure for the patient of Parkinson's disease and shape of the Lissajous figure for the healthy person may be calculated to catch this Lissajous figure. Concretely, as shown in FIG. 26, the mean of the shortest distances with the template of the Lissajous figure for the healthy person in each point of Lissajous figure of the fingers tapping motion for one cycle of patient of Parkinson's disease are calculated. The average of the values about the Lissajous figure of whole measurement time is calculated. It may be said that if this value is big, the Lissajous figure for the patient of Parkinson's disease and the template of the Lissajous figure for the healthy person are very different. In addition, acceleration and speed are standardized with each largest amplitude in Lissajous figure, when this characteristics is calculated

[Effect]

Figure 27A:
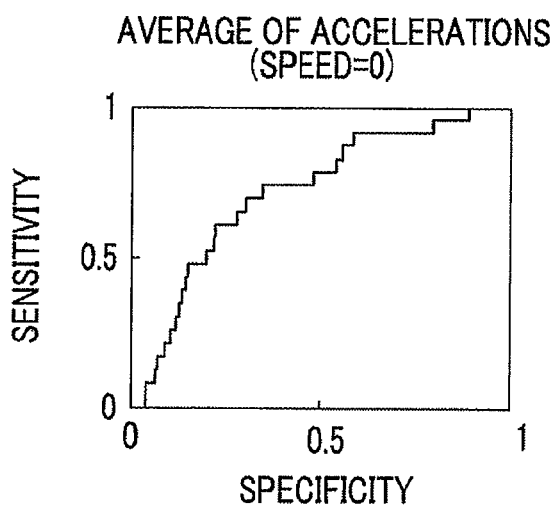
FIG. 27A-27C are the figures showing characteristics calculated from the Lissajous figure.
Figure 27B:
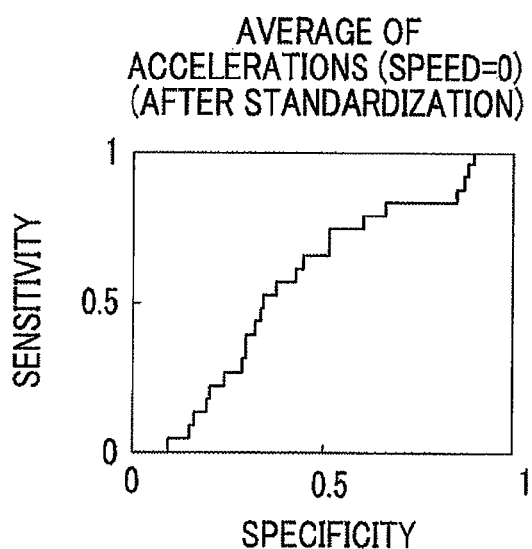
Figure 27C:
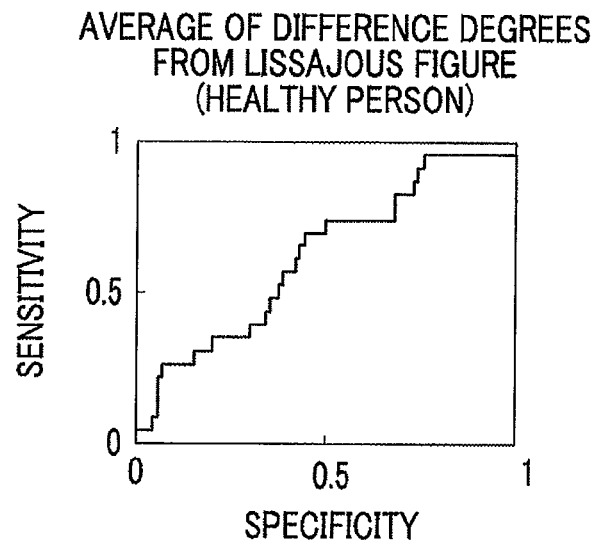

FIG. 27A is the figure showing ROC curve about average of minimums of acceleration at point of speed=0 in the Lissajous figure. FIG. 27B is the figure showing ROC curve about average (after standardization) of minimums of acceleration at point of speed=0 in the Lissajous figure. FIG. 27C is the figure showing ROC curve about difference degree with Lissajous figure (patient of Parkinson's disease) and Lissajous figure (healthy person).

From values of AUC and so on in the FIG. 27A-27C, it may be said that these characteristics are effective to distinguish motion disorder group from healthy person group and can be used for characteristics for calculation of the MDSV. In addition, about these characteristics, the revision by age performed in the first embodiment is not performed.

(Fourth Embodiment)

With reference to the drawings will be described a fourth embodiment of the invention in detail below. In the fourth embodiment, an application example of this invention to the Parkinson's disease will be described, like the case of the first embodiment. In addition, because FIG. 1-4, FIG. 6-15B, FIG. 18, FIG. 19 are similar to the first embodiment, those explanation is omitted.

[Calculation Method of the Characteristics]

Figure 28:
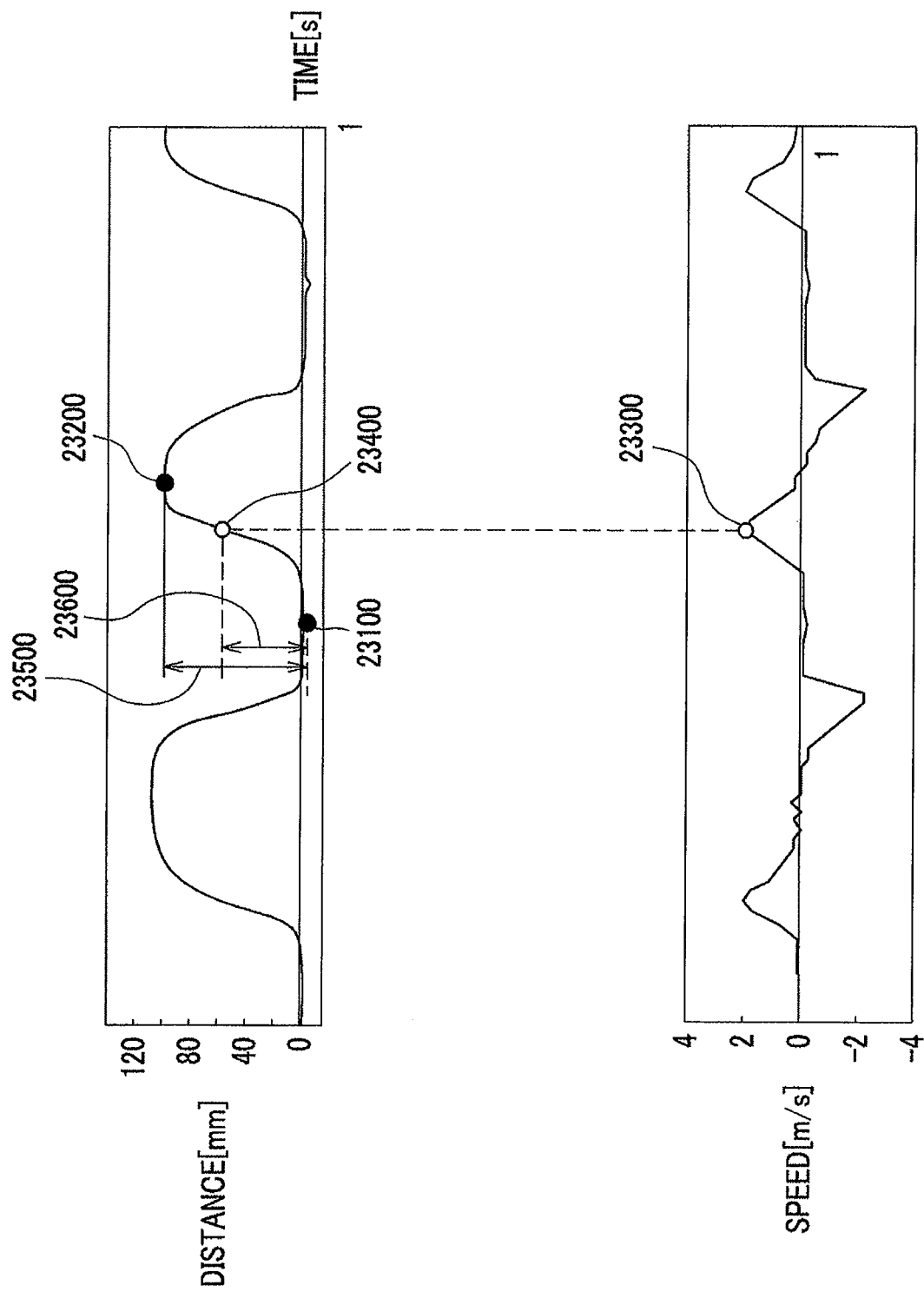
FIG. 28 is the figure for describing calculation of the distance at the maximum opening speed.

For characteristics that the characteristics generating section 1222 (see FIG. 1) generates, a distance at the time of maximum opening speed is calculated. The calculation method of this characteristics will be described as follows. As shown in FIG. 28, a point 23300 at which speed becomes maximum and a distance 23400 at that time in opening motion (range from local minimum value 23100 of the distance waveform to maximum value 23200 of distance waveform appearing for the first time next) are calculated. And difference 23600 of distance 23400 and local minimum 23100 are divided by difference 23500 of maximum value 23200 and local minimum 23100. The calculated characteristics is the mean or standard deviation of this value in whole measurement time.

Figure 29:
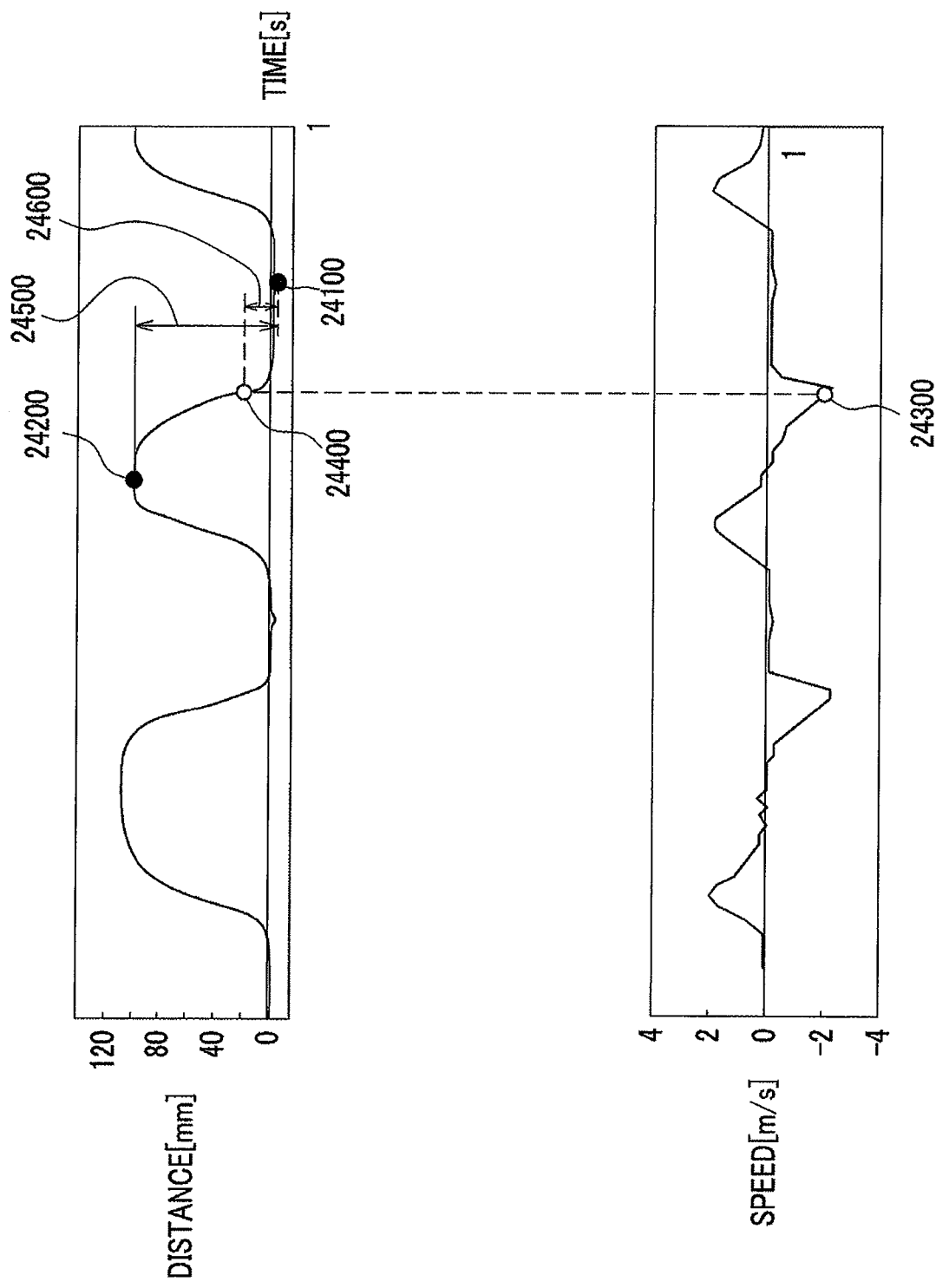
FIG. 29 is the figure for describing calculation of the distance at the minimum closing speed.

Likewise, as shown in FIG. 29, point 24300 at which speed becomes minimum and distance 24400 at that time in closing motion (range from local maximum value 24200 of the distance waveform to minimum value 24100 of distance waveform appearing for the first time next) are calculated. And difference 24600 of distance 24400 and local minimum value 24100 are divided by difference 24500 of maximum value 24200 and local minimum value 24100. The calculated characteristics is the mean or standard deviation of this value in whole measurement time.

In the case of a healthy person, because the control of the muscular strength is easy, a timing of the maximum speed in the opening motion is the almost same (it is similar about the closing motion). On the other hand, in the case of a patient of Parkinson's disease, because the control of the muscular strength is difficult, a timing of the maximum speed in the opening motion/is different (it is similar about the closing motion). By such a property, high performance to distinguish healthy person from the patient of Parkinson's disease is realized by using characteristics described above. In other words, this characteristics can be used for characteristics for calculation of the MDSV.

[Effect]

In FIGS. 30A, 30B, 31A and 3B, "SENSITIVITY" is ratio in which it was decided that the person was a patient precisely about all patient of Parkinson's disease. In other words, if "SENSITIVITY" is high, the possibility that it is misdecided that a patient of Parkinson's disease is a healthy person is low.

In addition, "SPECIFICITY" is ratio that it was decided in which the person was a healthy person precisely about all healthy persons. In other words, if "SPECIFICITY" is high, the possibility that it is misdecided that a healthy person is a patient of Parkinson's disease is low.

In FIGS. 30A, 30B, 31A and 31B, the folded lines are ROC curves, and estimation object is healthy person group (A) and motion disorder person group (A) shown in FIG. 19. In addition, about these characteristics, the revision by age performed in the first embodiment is not performed. As shown in FIGS. 30A, 30B, 31A and 31B, AUC of standard deviation of distances at maximum opening speed and AUC of standard deviation of distances at minimum closing speed are high. Therefore, if those standard deviations are used, motion disorder group can be distinguished from healthy person group well.

In addition, in each embodiment, it can be made program to let a computer constituting the motor function estimating system 1000 carry it out. The computer installed the program in can realize each function based on the program.

The explanation of the embodiments will be over. However, the state of this invention is not limited to these. For example, a weight coefficient may be added to each age-normalized characteristics, when plural age-normalized characteristics are composed, and MDSV is generated. For example, the weight coefficient is coefficient based on a value of AUC, or weight coefficient that is most suitable for distinguishing motion disorder person group from healthy person group, was calculated beforehand based on past information by statistical technique.

In addition, the motor function estimating system 1000 may be realized by one computer, and by computers more than two. In addition, in the range that does not deviate from a purpose of this invention, concrete constitution and processing may be changed.

What is claimed is:

1. A motor function estimating system comprising:
a memory unit for storing waveform data with reference to a time of a fingers tapping motion; the waveform data is obtained by a motion sensor attached to a subject person who does the fingers tapping motion that is repetition of an opening and closing motion of two fingers of one hand;

an analyzing section for analyzing the waveform data stored in the memory unit; and a display unit for displaying an analysis result by the analyzing section;

wherein the analyzing section comprises:

a motion waveform generating section for making a motion waveform corresponding to the waveform data stored in the memory unit;

a characteristics generating section for making plural characteristics that represent features of the fingers tapping motion, based on the motion waveform;

an age-normalized characteristics generating section for creating each of plural age-normalalized characteristics by calculation a regression line or a regression curve that represents a distribution tendency depending on age of each of the plural characteristics and calculating a difference between each of the plural characteristics and a value of the age on the regression line or the regression curve;

a motion disorder synthesis value generating section for creating a motion disorder synthesis value that represents a degree of motion disorder of the subject person by comparing the plural age-normalized characteristics made by the age-normalized characteristics generating section with corresponding characteristics of healthy persons previously stored in the memory unit and synthesizing the plural characteristics.

2. The motor function estimating system according to claim 1, wherein the characteristics generating section calculates time for which two fingers are in contact as the characteristics by using a local maximum point and local minimum value of waveform data about acceleration of the fingers tapping motion and a local maximum point and local minimum value of waveform data about jerk which is provided by differentiating the waveform data about acceleration.

3. The motor function estimating system according to claim 1, wherein the characteristics generating section calculates a similarity degree of a Lissajous figure for the subject person and a Lissajous figure for healthy persons, the Lissajous figure being a dimensional image created from speed data and acceleration data of the fingers tapping motion as the characteristics.

4. The motor function estimating system according to claim 1, wherein the characteristics generating section calculates, as the characteristics, a first statistical indicator value from a distance waveform of the fingers tapping motion when speed data of the fingers tapping motion become a local maximum value and a second statistical indicator value from a distance waveform of the fingers tapping motion when the speed data of the fingers tapping motion become a local minimum value.

5. The motor function estimating system according to claim 1, wherein the analyzing section includes a motion disorder score estimating section for estimating a motion disorder score that represents a score of disease severity of a motion disorder from the motion disorder synthesis value by using a predetermined approximation function that shows relation of the motion disorder synthesis value and the motion disorder score.

6. The motor function estimating system according to claim 1, wherein the motion disorder synthesis value generating section selects the characteristics having high value of AUC (Area Under a Receiver Operating Characteristic (ROC) Curve) if there are plural characteristics corresponding to any symptom of a motion disorder, and obtains the motion disorder synthesis value by multiplying the selected characteristics by a weight coefficient based on the value of the AUC and synthesizing the plural characteristics.

7. The motor function estimating system according to claim 6, wherein the motion disorder synthesis value generating section normalizes each of the plural characteristics by using a distribution of healthy person group, and averages an absolute value of the normalized plural characteristics as the motion disorder synthesis value.

8. The motor function estimating system according to claim 6, wherein the motion disorder synthesis value generating section synthesizes the plural characteristics by applying best weight coefficients to distinguish a healthy person data group from a motion disorder person data group, wherein the best weight coefficients are calculated in advance by applying statistical techniques to past information of each of the plural characteristics.

9. The motor function estimating system according to claim 1, wherein the display unit displays each of the plural characteristics used to make the motion disorder synthesis value with a radar chart image.

10. A motor function estimating method comprising the steps of:

storing waveform data with reference to a time of a fingers tapping motion in a memory unit; wherein the waveform data is obtained by a motion sensor attached to a subject person who does the fingers tapping motion that is repetition of an opening and closing motion of two fingers of one hand;

analyzing the waveform data stored in the memory unit in an analyzing section; and displaying an analysis result by the analyzing section on a display unit;

the analyzing step comprising:

generating, in a motion waveform generating section, a motion waveform corresponding to the waveform data stored in the memory unit;

generating, in a characteristics generating section, plural characteristics that represent features of the fingers tapping motion, based on the motion waveform;

generating, in an age-normalized characteristics generating section, each of plural age-normalized characteristics by calculating a regression line or a regression curve that represents a distribution tendency depending on age of each of the plural characteristics and calculating a difference between each of the plural characteristics and a value of the age on the regression line or the regression curve, and generating, in a motion disorder synthesis value generating section, a motion disorder synthesis value that represents a degree of motion disorder of the subject person by comparing the plural age-normalized characteristics made by the age-normalized characteristics generating section with corresponding characteristics of healthy persons previously stored in the memory unit and synthesizing the plural characteristics.

11. The motor function estimating method according to claim 10, further comprising the step of calculating, in the characteristics generating section, a time for which two fingers are in contact as the characteristics by using a local maximum point and a local minimum value of waveform data about acceleration of the fingers tapping motion and a local maximum point and a local minimum value of waveform data about jerk which is provided by differentiating the waveform data about acceleration.

12. The motor function estimating method according to claim 10, further comprising the step of calculating, in the characteristics generating section, a similarity degree of a Lissajous figure for the subject person and a Lissajous figure for healthy persons, the Lissajous figure being a two dimensional image created from speed data and acceleration data of the fingers tapping motion as the characteristics.

13. The motor function estimating method according to claim 10, further comprising the step of calculating, in the characteristics generating section, a first statistical indicator value on the value in a distance waveform of the fingers tapping motion when speed data of the fingers tapping motion become a local maximum value as the characteristics, and a second statistical indicator value from a distance waveform of the fingers tapping motion when the speed data of the fingers tapping motion become a local minimum value as the characteristics.

14. The motor function estimating method according to claim 10, wherein the analyzing step further comprises estimating, in a motion disorder score estimating section, a motion disorder score that represents a score of disease severity of a motion disorder from the motion disorder synthesis value by using a predetermined approximation function that shows relation of the motion disorder synthesis value and the motion disorder score.

15. The motor function estimating method according to claim 10, wherein the step of generating a motion disorder synthesis value further comprises selecting the characteristics having high value of AUC (Area Under a Receiver Operating Characteristic (ROC) Curve) if there are plural characteristics corresponding to any symptom of a motion disorder, and obtaining the motion disorder synthesis value by multiplying the selected characteristics by a weight coefficient based on the value of the AUC and synthesizing the plural characteristics.

* * * * *